US010495590B2

(12) United States Patent
Vecchio et al.

(10) Patent No.: US 10,495,590 B2
(45) Date of Patent: Dec. 3, 2019

(54) METHODS OF SELECTING MATERIAL COMPOSITIONS AND DESIGNING MATERIALS HAVING A TARGET PROPERTY

(71) Applicant: Scoperta, Inc., San Diego, CA (US)

(72) Inventors: Kenneth Vecchio, San Diego, CA (US); Justin Lee Cheney, Encinitas, CA (US)

(73) Assignee: Scoperta, Inc., San Diego, CA (US)

( * ) Notice: Subject to any disclaimer, the term of this patent is extended or adjusted under 35 U.S.C. 154(b) by 132 days.

(21) Appl. No.: 15/887,867

(22) Filed: Feb. 2, 2018

(65) Prior Publication Data

US 2018/0172611 A1    Jun. 21, 2018

Related U.S. Application Data

(63) Continuation of application No. 14/512,115, filed on Oct. 10, 2014, now Pat. No. 10,345,252.
(Continued)

(51) Int. Cl.
*G01N 25/18*  (2006.01)
*B01F 3/18*   (2006.01)
(Continued)

(52) U.S. Cl.
CPC ............. *G01N 25/18* (2013.01); *B01F 3/188* (2013.01); *G16C 20/30* (2019.02); *G01D 21/00* (2013.01);
(Continued)

(58) Field of Classification Search
CPC .......... G01N 25/18; G16C 20/30; B01F 3/188
(Continued)

(56) References Cited

U.S. PATENT DOCUMENTS 2,043,952 A    6/1936  Ffield
2,156,306 A    5/1939  Rapatz
(Continued)

FOREIGN PATENT DOCUMENTS

CA    2927074 A    4/2015
CN    102686762    3/2014
(Continued)

OTHER PUBLICATIONS

Arroyave, Raymundo: "Commentary: Recent Advances in Ab Initio Thermodynamics of Materials", TMS, vol. 65, No. 11, 2013, Oct. 1, 2013 (Oct. 1, 2013), pp. 1499-1500, DOI: 10.1007/s11837-013-0744-7.
(Continued)

*Primary Examiner* — Eman A Alkafawi
(74) *Attorney, Agent, or Firm* — Knobbe, Martens, Olson & Bear LLP

(57) ABSTRACT

The disclosed technology relates to a method of selecting a material composition and/or designing an alloy. In one aspect, a method of selecting a composition of a material having a target property comprises receiving an input comprising thermodynamic phase data for a plurality of materials. The method additionally includes extracting from the thermodynamic phase data a plurality of thermodynamic quantities corresponding to each of the materials by a computing device. The extracted thermodynamic quantities are predetermined to have correlations to microstructures associated with physical properties of the material. The method additionally includes storing the extracted thermodynamic quantities in a computer-readable medium. The method further includes electronically mining the stored thermodynamic quantities using the computing device to rank at least a subset of the materials based on a comparison
(Continued)

of at least a subset of the thermodynamic quantities that are correlated to the target property.

20 Claims, 12 Drawing Sheets

Related U.S. Application Data

(60) Provisional application No. 61/917,845, filed on Dec. 18, 2013, provisional application No. 61/889,413, filed on Oct. 10, 2013.

(51) Int. Cl.
| | | |
|---|---|---|
| G16C 20/30 | (2019.01) | |
| G01N 33/00 | (2006.01) | |
| G06F 17/40 | (2006.01) | |
| G01D 21/00 | (2006.01) | |
| G16C 20/70 | (2019.01) | |
| G06F 19/00 | (2018.01) | |

(52) U.S. Cl.
CPC ...... *G01N 2033/0003* (2013.01); *G06F 17/40* (2013.01); *G06F 19/00* (2013.01); *G16C 20/70* (2019.02)

(58) Field of Classification Search
USPC .......................................................... 702/30
See application file for complete search history.

(56) References Cited

U.S. PATENT DOCUMENTS

| | | | |
|---|---|---|---|
| 2,936,229 | A | 5/1960 | Shepard |
| 3,024,137 | A | 3/1962 | Witherell |
| 3,181,970 | A | 5/1965 | Witherell et al. |
| 3,448,241 | A | 6/1969 | Penson et al. |
| 3,554,792 | A | 1/1971 | Johnson |
| 3,650,734 | A | 3/1972 | Kantor et al. |
| 3,765,956 | A | 10/1973 | Li |
| 3,843,359 | A | 10/1974 | Fiene et al. |
| 3,859,060 | A | 1/1975 | Eiselstein et al. |
| 3,975,612 | A | 8/1976 | Nakazaki et al. |
| 4,010,309 | A | 3/1977 | Peterson |
| 4,017,339 | A | 4/1977 | Okuda et al. |
| 4,042,383 | A | 8/1977 | Petersen et al. |
| 4,415,530 | A | 11/1983 | Hunt |
| 4,639,576 | A | 1/1987 | Shoemaker et al. |
| 4,762,681 | A | 8/1988 | Tassen et al. |
| 4,822,415 | A | 4/1989 | Dorfman et al. |
| 4,981,644 | A | 1/1991 | Chang |
| 5,306,358 | A | 4/1994 | Lai et al. |
| 5,357,443 | A | 10/1994 | Watanbe et al. |
| 5,375,759 | A | 12/1994 | Hiraishi et al. |
| 5,618,451 | A | 4/1997 | Ni |
| 5,820,939 | A | 10/1998 | Popoola et al. |
| 5,858,893 | A | 1/1999 | Yamamoto |
| 5,861,605 | A | 1/1999 | Ogawa et al. |
| 5,935,350 | A | 8/1999 | Raghu et al. |
| 6,038,514 | A | 3/2000 | Nozaki |
| 6,210,635 | B1 | 4/2001 | Jackson et al. |
| 6,251,492 | B1 | 6/2001 | Tomie |
| 6,398,103 | B2 | 6/2002 | Hasz et al. |
| 6,441,334 | B1 | 8/2002 | Aida et al. |
| 6,608,286 | B2 | 8/2003 | Jiang |
| 6,613,162 | B1 | 8/2003 | Dutta et al. |
| 6,647,342 | B2 | 11/2003 | Iglesia et al. |
| 6,702,906 | B2 | 3/2004 | Ogawa et al. |
| 6,750,430 | B2 | 6/2004 | Kelly |
| 6,799,089 | B2 | 9/2004 | Toulhoat et al. |
| 6,858,103 | B2 * | 2/2005 | Wolverton ............... C22F 1/00 148/502 |
| 6,974,976 | B2 | 12/2005 | Hollars |
| 7,285,151 | B2 | 10/2007 | Sjodin et al. |
| 7,292,958 | B2 | 11/2007 | Ceder et al. |
| 7,361,411 | B2 | 4/2008 | Daemen et al. |
| 7,411,682 | B2 | 8/2008 | Moshe |
| 7,491,910 | B2 | 2/2009 | Kapoor et al. |
| 7,569,286 | B2 | 8/2009 | Daemen et al. |
| 7,776,451 | B2 | 8/2010 | Jiang et al. |
| 7,909,505 | B2 | 3/2011 | Alexandrov et al. |
| 7,935,198 | B2 | 5/2011 | Branagan et al. |
| 8,153,935 | B2 | 4/2012 | Jang et al. |
| 8,187,725 | B2 | 5/2012 | Kiser et al. |
| 8,192,682 | B2 | 6/2012 | Maziasz et al. |
| 8,301,286 | B2 | 10/2012 | Babu |
| 8,498,728 | B2 | 7/2013 | Conrardy et al. |
| 8,562,759 | B2 | 10/2013 | Cheney et al. |
| 8,562,760 | B2 | 10/2013 | Cheney et al. |
| 8,640,941 | B2 | 2/2014 | Cheney |
| 8,647,449 | B2 | 2/2014 | Cheney et al. |
| 2001/0019781 | A1 | 9/2001 | Hasz |
| 2002/0148533 | A1 | 10/2002 | Kim et al. |
| 2004/0062677 | A1 | 4/2004 | Chabenat et al. |
| 2004/0063320 | A1 | 4/2004 | Hollars |
| 2004/0079742 | A1 | 4/2004 | Kelly |
| 2004/0115086 | A1 | 6/2004 | Chabenat et al. |
| 2004/0230411 | A1 | 11/2004 | Zheng et al. |
| 2005/0076092 | A1 | 8/2005 | Seimens |
| 2006/0074594 | A1 | 4/2006 | Ceder |
| 2006/0191606 | A1 | 8/2006 | Ogawa et al. |
| 2007/0029295 | A1 | 2/2007 | Branagan |
| 2007/0090167 | A1 | 4/2007 | Arjakine et al. |
| 2007/0284018 | A1 | 12/2007 | Hamano et al. |
| 2008/0031769 | A1 | 2/2008 | Yeh |
| 2008/0149397 | A1 | 6/2008 | Branagan |
| 2008/0241580 | A1 | 10/2008 | Kiser et al. |
| 2009/0017328 | A1 | 1/2009 | Katoh et al. |
| 2009/0053100 | A1 | 2/2009 | Pankiw et al. |
| 2009/0258250 | A1 | 10/2009 | Daemen et al. |
| 2009/0285715 | A1 | 11/2009 | Arjakine et al. |
| 2010/0009089 | A1 | 1/2010 | Junod et al. |
| 2010/0044348 | A1 | 2/2010 | Buchmann |
| 2010/0068114 | A1 | 3/2010 | Veinot |
| 2010/0101780 | A1 | 4/2010 | Ballew et al. |
| 2010/0121472 | A1 | 5/2010 | Babu |
| 2010/0166594 | A1 | 7/2010 | Hirata et al. |
| 2010/0189588 | A1 | 7/2010 | Kawatsu et al. |
| 2011/0064963 | A1 | 3/2011 | Cheney et al. |
| 2011/0100720 | A1 | 5/2011 | Branagan et al. |
| 2011/0139761 | A1 | 6/2011 | Sugahara et al. |
| 2011/0171485 | A1 | 7/2011 | Kawamoto et al. |
| 2012/0055903 | A1 | 3/2012 | Izutani et al. |
| 2012/0156020 | A1 | 6/2012 | Kottilingam et al. |
| 2012/0160363 | A1 | 6/2012 | Jin et al. |
| 2012/0288400 | A1 | 11/2012 | Hirata et al. |
| 2013/0085589 | A1 | 4/2013 | Conrardy |
| 2013/0094900 | A1 | 4/2013 | Folkmann et al. |
| 2014/0006531 | A1 | 3/2014 | Cheney |
| 2014/0105780 | A1 | 4/2014 | Cheney |
| 2014/0161984 | A1 | 6/2014 | Cheney |
| 2014/0219859 | A1 | 8/2014 | Cheney |
| 2014/0248509 | A1 | 9/2014 | Cheney |
| 2016/0034614 | A1 | 2/2016 | Wang |

FOREIGN PATENT DOCUMENTS

| | | |
|---|---|---|
| CN | 103635284 | 3/2014 |
| CN | 104039483 | 9/2014 |
| CN | 105814570 | 7/2016 |
| DE | 27 54 437 | 7/1979 |
| DE | 33 20 513 | 12/1983 |
| EP | 0 365 884 | 5/1990 |
| EP | 1 338 663 | 8/2003 |
| EP | 2 305 415 | 8/2003 |
| EP | 3055802 | 8/2016 |
| JP | 58-132393 | 8/1983 |
| JP | 60-133996 A | 7/1985 |
| JP | 63-026205 A | 2/1988 |
| JP | 03-133593 A | 6/1991 |
| JP | 2008/007809 | 1/2008 |
| WO | WO 2005/076092 A1 | 8/2005 |
| WO | WO 2006/086350 | 8/2006 |

(56) References Cited

FOREIGN PATENT DOCUMENTS

| | | |
|---|---|---|
| WO | WO 2011/035193 | 3/2011 |
| WO | WO 2011/071054 | 6/2011 |
| WO | WO 2011/158706 | 12/2011 |
| WO | WO 2012/037339 | 3/2012 |
| WO | WO 2012/129505 | 9/2012 |
| WO | WO 2013/055652 A1 | 4/2013 |
| WO | WO 2013/101561 | 7/2013 |
| WO | WO 2013/133944 | 9/2013 |
| WO | WO 2014/059177 | 4/2014 |
| WO | WO 2015/054637 A1 | 4/2015 |
| ZA | 2013/02311 | 12/2013 |

OTHER PUBLICATIONS

ASTA: "Computational Materials Discovery and Design", JOM the Minerals, Metals &Materials Society, vol. 66, No. 3, 2014, pp. 364-365.

Branagan, et al.: "Developing extreme hardness (>15GPa) in iron based nanocomosites, Composites Part A: Applied Science and Manufacturing," Elsevier Science Publishers B.V., Amsterdam, NL, vol. 33, No. 6, Jun. 1, 2002, pp. 855-859.

Canadian Office Action dated Feb. 2, 2017 in corresponding Canadian Application No. 2,927,074.

Cheney, et al.: "Development of quaternary Fe-based bulk metallic glasses," Materials Science and Engineering, vol. 492, No. 1-2, Sep. 25, 2008, pp. 230-235.

Curtarolo S. et al. (Feb. 20, 2013) "The high-throughput highway to computational materials design," Nature Materials, vol. 12, No. 3, pp. 191-201.

Entel, Peter et al. "Interaction of Phase Transformation and Magnetic Properties of Heusler Alloys: A Density Functional Theory Study", The Minerals, Metals & Materials Society, vol. 65, No. 11, 2013, Sep. 26, 2013 (Sep. 26, 2013), pp. 1540-1549, DOI: 10.1007/s11837-013-0757-2.

Goune et al.: "Thermodynamic and structural studies on nirtide Fe-1.62%Mn and Fe-0.56%V alloys", Materials Science and Engineering A. vol. 351, No. 1-2, Jun. 1, 2003 (Jun. 1, 2003), pp. 23-30, XP055159786, ISSN: 0921-5093, DOI: 10.1026/S0921-5093(02)00277-0 p. 24, left hand column, lines 39-44 table 1.

Grobner J. et al, (2001) "Selection of promising quaternary candidates from Mg—Mn—(Sc, Gd, Y, Zr) for development of creep-resistant magnesium alloys," Journal of Alloys and Compounds, vol. 320, No. 2, pp. 296-301.

International Preliminary Report on Patentability in the International Application No. PCT/US2014/060140, dated May 20, 2016.

International Search Report and Written Opinon dated Jan. 8, 2015 in corresponding PCT Application No. PCT/US2014/060140.

Khalifa et al.: "Effect of Mo—Fe substitution on glass forming ability, thermal stability, and hardness of Fe—C—B—Mo—Cr—W bulk amorphous allows," Materials Science and Engineering, vol. 490, No. 1-2, Aug. 25, 2008, pp. 221-228.

Kim et al.: "Ab Initio Calculated Thermodynamic Properties of Mo5SiB2 Phase and Nb5SiB2 Phase", The Minerals, Metals & Matericals Society, vol. 65, No. 11, 2013, Oct. 5, 2013 (Oct. 5, 2013), pp. 1482-1486, DOI: 10.1007/s11837-013-0770-5.

Mohri: "Cluster Variation Method", TMS, vol. 65, No. 11, 2013, Aug. 29, 2013 (Aug. 29, 2013), pp. 1510-1522, DOI: 10.1007/s11837-013-0738-5.

Saal et. Al.: "Materials Design and Discovery with High-Throughput Density Functional Theory: The Open Quatum Materials Database (OQMD)", The Minerals, Metals & Materials Society, vol. 65, No. 11, 2013, Sep. 28, 2013 (Sep. 28, 2013), pp. 1501-1509, DOI: 10.1007/s11837-013-0755-4.

Tillack et al.: "Selection of Nickel, Nickel-Copper, Nickel-Cromium, and Nickel-Chromium-Iron Allows", AMS Handbook, Welding, Brazing and Soldering, vol. 6, Dec. 1, 1993 (Dec. 1, 1993) pp. 586-592, XP008097120, p. 589.

Turchi et al.: "From Electronic Structure to Thermodynamics of Actinide-Based Alloys", JOM the Minerals, Metals & Materials Society, vol. 66, No. 3, 2014, pp. 375-388.

Walle: "Methods for First-Principles Alloy Thermodynamics", The Minerals, Metals & Materials Society, vol. 65, No. 11, 2013, Oct. 4, 2013 (Oct. 4, 2013), pp. 1523-1532, DOI: 10.1007/s11837-013-0764-3.

Wang, Yi et al.: "Density Functional Theory-Based Database Development and CALPHAD Automation", The Minerals, Metals & Materials Society, vol. 65, No. 11, 2013, Sep. 12, 2013 (Sep. 12, 2013), pp. 1533-1539, DOI: 10.1007/s11837-013-0751-8.

Written Opinion of the International Preliminary Examining Authority for the International Application No. PCT/US2014/060140, dated Sep. 21, 2015.

Written Opinion of the International Preliminary Examining Authority for International Application No. PCT/US2014/060140, dated Feb. 23, 2016, date of receipt via fax of Feb. 18, 2016.

Zhang et al.: "Precipitation Simulation of AZ91 Alloy", JOM the Minerals, Metals & Materials Society, vol. 66, No. 3, 2014, pp. 389-396.

Zhu R. et al.: "Multi-phase microstructure design of a low-alloy TRIP-Assisted steel through a combined computational and experimental methodology", ACTA Materialia, Elsevier, Oxford, GB, col. 60, No. 6, Feb. 4, 2012 (Feb. 4, 2012), pp. 3022-3022, XP028476583, ISSN: 1359-6454, DOI: 10.1016/J.Actamat.2012.02.007 [retrieved on Feb. 20, 2012] abstract p. 3024, left hand column, line 35—p. 3025, left hand column, line 7 figures 1,2 table 1.

Zhuang et al.: "Computational Discovery, Characterization, and Design of Single-Layer Materials", JOMnerals, Metals & Materials Society, vol. 66, No. 3, 2014, pp. 366-374.

\* cited by examiner

METHODS OF SELECTING MATERIAL COMPOSITIONS AND DESIGNING MATERIALS HAVING A TARGET PROPERTY

CROSS-REFERENCE TO RELATED APPLICATION

This application is a continuation of U.S. application Ser. No. 14/512,115, filed Oct. 10, 2014, which claims the benefit of U.S. Provisional Application No. 61/917,845, filed Dec. 18, 2013, and U.S. Provisional Application No. 61/889,413, filed Oct. 10, 2013, the entireties of which are hereby incorporated by reference.

BACKGROUND

Field of the Invention

The disclosed technology relates in some embodiments to designing materials, and more particularly to designing alloys using thermodynamic phase diagrams. The disclosed technology also relates to selecting compositions of materials, and more particularly to selecting compositions of a material having a target property by using thermodynamic quantities extracted from thermodynamic phase data.

Description of the Related Technology

Selecting a material having a target property for manufacturing often requires a manufacturer to have an understanding of the microstructure and/or the nanostructure that is associated with the target property. For some material systems, equilibrium thermodynamics can be used to predict the presence of various phases of a material system under equilibrium conditions. For example, an equilibrium phase diagram can be used to describe physical conditions under which various equilibrium phases of a material system can be stable and under which some equilibrium phases can coexist. Generation of the phase diagrams, however, especially for material systems having many (e.g., greater than four) elements with at least as many phases, is often computation-intensive. In addition, when many material systems are compared for designing a material system, computation and comparison of the phase diagrams can be prohibitively costly in terms of both computing and human resources. Furthermore, extraction of useful information often involves a skilled artisan to interpret a graphical representation, which can also be time-consuming.

Furthermore, while thermodynamic phase diagrams provide equilibrium phase information, they may not necessarily correlate to actual phases present because the phase diagrams do not contain information related to kinetics of formation of the phases and/or information related to energetics related to the microstructure of the materials. While kinetics and/or microstructural information can be gathered using physical and microstructural analysis techniques such as, for example, electron beam and X-ray imaging and composition analysis techniques, such techniques are also often time consuming and/or cost-prohibitive.

In a manufacturing environment, to select a material composition having a target property, a material designer can typically analyze a graphical phase diagram to identify equilibrium phases that may be desirable, synthesize a limited number of samples based on the analysis, and subsequently perform physical analyses such as electron microscopy and composition analysis before choosing the material composition to be scaled up for manufacturing. Such a serial process can be prohibitively expensive and time consuming because the material designer is involved in the analysis of each graphical phase diagram and/or physical analysis data to verify whether the synthesized samples do indeed have the desired phases in the desired amount and in the desired microstructural form, especially when the material system is complex (e.g., has over four elements and phases) and many compositions (e.g., hundreds or thousands) are to be evaluated for several target properties. Thus, there is a need for a high throughput method for selecting a material having a target property that is at least partly computer-implemented such that the involvement of the material designer can be reduced and eliminated altogether in some portions of the overall selection process.

SUMMARY

In one aspect, a method of selecting a composition of a material having a target property comprises receiving an input comprising thermodynamic phase data for a plurality of materials. The method additionally includes extracting from the thermodynamic phase data a plurality of thermodynamic quantities corresponding to each of the materials by a computing device. The extracted thermodynamic quantities are predetermined to have correlations to microstructures associated with physical properties of the material. The method additionally includes storing the extracted thermodynamic quantities in a computer-readable medium, e.g., a non-transient computer-readable medium. The method further includes electronically mining the stored thermodynamic quantities using the computing device to rank at least a subset of the materials based on a comparison of at least a subset of the thermodynamic quantities that are correlated to the target property.

In another aspect, a material composition selection apparatus comprises a thermodynamic phase data extraction module configured to receive an input comprising thermodynamic phase data for a plurality of materials and configured to extract therefrom a plurality of thermodynamic quantities corresponding to each of the materials by a computing device. A computing device comprising a processor may also be part of the material composition selection apparatus. The extracted thermodynamic quantities are predetermined to have correlations to microstructures associated with physical properties of the material. The apparatus may additionally include a storage module comprising a non-transitory or a non-transitory medium having stored thereon the extracted thermodynamic quantities. The apparatus further includes an electronic data mining module configured to electronically mine the stored thermodynamic quantities using the computing device to rank at least a subset of the materials based on a comparison of at least a subset of the thermodynamic quantities that are correlated to the target property.

In yet another aspect, a non-transitory computer-readable medium comprises instructions stored thereon that when executed cause a computing device to perform the following steps: receiving an input comprising thermodynamic phase data for a plurality of materials; extracting from the thermodynamic phase data a plurality of thermodynamic quantities corresponding to each of the materials by the computing device, wherein the extracted thermodynamic quantities are predetermined to have correlations to microstructures associated with physical properties of the material; storing the extracted numerical quantities in a computer-readable medium; and electronically mining the stored thermodynamic quantities using the computing device to rank at least a subset of the materials based on a comparison of at least a subset of the thermodynamic quantities that are correlated to the target property.

In yet another aspect, a method of designing a material or an alloy is provided, for example a method for designing a material having a target property. The method comprises calculating thermodynamic phase diagrams for a plurality of materials or alloys using a processor comprising logic circuitry. The method additionally comprises extracting from the phase diagrams numerical thermodynamic quantities corresponding to each of the plurality of materials or alloys. The method further comprises storing the numerical quantities in an electronic database. The method further comprises electronically mining the electronic database or the stored numerical quantities with a processor to rank the materials or the alloys. The ranking may be based on a comparison of the numerical quantities for different alloy compositions, or the ranking may be based on a comparison of at least a subset of the numerical quantities for each material against a material design criteria corresponding to the target property.

In some embodiments of the method above, the thermodynamic phase diagrams are calculated to determine equilibrium mole fractions of thermodynamically stable phases as a function of temperature. In some embodiments, the extracting step is based on a set of predetermined thermodynamic evaluation criteria. Extracting the thermodynamic quantities may comprise extracting a solidification temperature of at least one thermodynamically stable phase. Extracting the thermodynamic quantities may comprise extracting a phase transition temperature from a first phase to a second phase. Extracting the phase transition temperature may include extracting a temperature at which a first rate of change of mole fraction of the first phase as a function of temperature is negative and a second rate of change of mole fraction of the second phase as a function of temperature is positive. Extracting the thermodynamic quantities comprises extracting an equilibrium mole fraction of at least one thermodynamically stable phase at a temperature between about 0° C. and 150° C. Extracting the thermodynamic quantities may comprise extracting a melting temperature, wherein extracting the melting temperature includes extracting a temperature at which a first rate of change of mole fraction of at least one thermodynamically stable phase is negative and a second rate of change of mole fraction of a liquid phase as a function of temperature is positive.

In some embodiments of the method above, electronically mining may comprise ranking the materials or alloys based on a comparison of solidification temperatures of at least two thermodynamically stable phases. Electronically mining may comprise ranking the materials or alloys based on a comparison of a phase transition temperature from a first phase to a second phase against at a solidification temperature of a third phase.

In some embodiments of the method above, storing the numerical quantities may comprise storing in a nonvolatile memory coupled to a processor. Storing the numerical quantities may comprise storing in a volatile memory coupled to a processor. Storing the numerical quantities may comprise storing in a removable memory medium.

In some embodiments of the method above, the properties of the materials or alloys may comprise microstructural properties. The method may be performed using a computer system comprising a plurality of processors. The entire method may performed using a computer system. The method may further comprise outputting information regarding the ranking of the materials or alloys. This information may be output to a display or to a computer-readable medium. The method may further comprise outputting a sub-set of materials or alloys having desired properties based on the ranking. The method may further comprise manufacturing one or more materials or alloys from the sub-set of alloys.

In other aspects, a method of designing an alloy need not include steps of calculating thermodynamic phase diagrams, extracting thermodynamic quantities from the phase diagrams, and storing quantities in an electronic database. In one aspect, a method of designing an alloy may comprise electronically mining an electronic database that includes numerical quantities corresponding to properties of alloys that were previously derived from thermodynamic phase diagrams for said alloys, wherein electronically mining is performed with a processor to rank the alloys based on a comparison of the numerical quantities for different alloy compositions.

In yet another aspect, a method for designing a material having a target property, comprising executing one or more instances of a thermodynamic phase diagram calculation algorithm for a plurality of materials using a processor comprising logic circuitry. The method further comprises executing one or more instances of a data extraction algorithm using a processor comprising logic circuitry, wherein executing the one or more instances of the data extraction algorithm comprises taking as input at least a subset of results from executing the one or more instances of the thermodynamic phase diagram calculation algorithm. The method further comprises storing results from executing the one or more instances of the data extraction algorithm in an electronic database. The method further comprises executing one or more instances of a data mining algorithm using a processor comprising logic circuitry, wherein executing the one or more instances of the data mining algorithm comprises taking as input at least a subset of the stored results from executing the one or more instances of the data extraction algorithm.

In some embodiments of the method above, executing the one or more instances of the data extraction algorithm comprises extracting from the at least a subset of results from executing the one or more instances of the thermodynamic phase diagram calculation algorithm a set of numerical thermodynamic quantities corresponding to each of the plurality of materials, wherein extracting is based on a set of predetermined thermodynamic evaluation criteria. The results from executing the one or more instances of the data extraction algorithm may include a spreadsheet including numerical thermodynamic quantities corresponding to each of the plurality of materials. Storing results may include storing in a nonvolatile storage media. Executing the one or more instances of data mining algorithm may include electronically mining the stored results with a processor to rank the materials based on a comparison of at least a subset of the numerical quantities for each material against a material design criteria corresponding to the target property. One of the processors for executing the one or more instances of the thermodynamic phase diagram calculation algorithm, the data extraction algorithm, or the data mining algorithm may be different from the remaining ones of the processors. Executing one or more instances of a data mining algorithm may be performed multiple times from the stored results.

Other aspects of this disclosure include further computer-implemented methods related to designing an alloy, as well as systems and apparatuses related to the same, as well as methods of manufacturing an alloy and the alloys manufactured themselves.

DETAILED DESCRIPTION

Calculation of thermodynamic phase diagrams for selecting a material composition is common practice in the field of metallurgy and materials science, and its use, aided by recent advances in computing power, has developed into a separate field of calculation techniques known in the industry as Calculation of Phase Diagrams (CALPHAD). The CALPHAD technique is very useful in aiding the understanding of alloys and in the design of new alloys. The output of the CALPHAD technique is a diagram displaying certain thermodynamic information such as, e.g., an equilibrium phase diagram which plots, e.g., percent fraction of phases of a material versus temperature. The displayed diagram is a graphical representation of the material's thermodynamic information or a plurality of materials' thermodynamic information. The diagram can be used by a skilled artisan to understand alloy systems under equilibrium and to design alloys based on such understanding.

Despite the advances in calculating thermodynamic phase diagrams to quantitatively determine the thermodynamic stability and the presence of equilibrium phases, as described above, generating and interpreting the phase diagrams, as well as correlating the results to microstructures associated with a physical property, can be prohibitively time consuming and/or expensive, especially for complex material systems involving many elements (e.g., greater than four) and complex microstructures. Disclosed herein are embodiments that describe methods whereby thermodynamic information can be effectively used in such a way that an alloy can be designed without a need to repetitively calculate phase diagrams and/or extract thermodynamic quantities therefrom, nor a need to resort to graphically represented phase diagrams, as is often done by a skilled artisan in the industry. Instead, the disclosed embodiments illustrate generating an alloy database of thermodynamic quantities created from automated algorithms. Subsequent to generation and storage of the thermodynamic quantities in a storage medium, the thermodynamic quantities can be mined by ranking and sorting to select candidates with predetermined correlation to microstructures associated with a physical property. Advantageously, the mining process can be performed repeatedly using automated algorithms, such that many alloys having various target physical properties can be designed using the mining process, without having to further calculate or resort to the phase diagrams or any other graphical display of phase data. The methods described herein are advantageous in providing rapid material design, because they can eliminate the need for a skilled artisan to evaluate a thermodynamic phase diagram and/or the need to extract thermodynamic quantities therefrom each time selection of a material having a new target property is desired.

Figure 1:
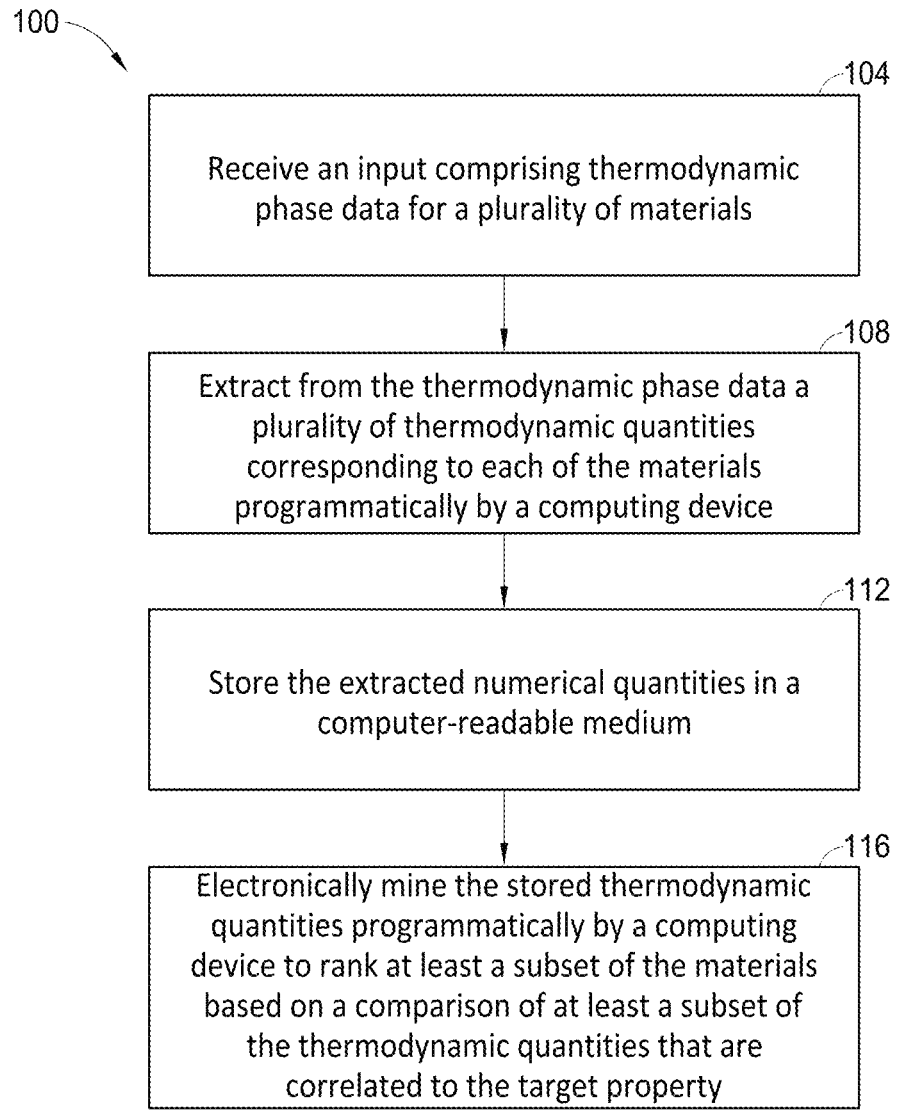
FIG. 1 is a flowchart illustrating a method of selecting a composition of a material having a target property, according to one embodiment.

FIG. 1 is a flowchart illustrating a method of selecting a composition of a material having a target property, according to one embodiment. The method 100 of selecting a composition of a material having a target property comprises, at a process 104, receiving an input comprising thermodynamic phase data for a plurality of materials. The method 100 additionally includes, at a process 108, extracting from the thermodynamic phase data a plurality of thermodynamic quantities corresponding to each of the materials using a microprocessor. The extracted thermodynamic quantities may be numerical quantities extracted directly from thermodynamic phase data, or numerical quantities that are derived from the directly extracted quantities. The extracted thermodynamic quantities are predetermined to have correlations to microstructures associated with physical properties of the material. The method 100 additionally includes, at a process 112, storing the extracted thermodynamic quantities in a computer-readable medium. The method 100 further includes, at a process 116, electronically mining the stored thermodynamic quantities using a microprocessor to rank at least a subset of the materials based on a comparison of at least a subset of the thermodynamic quantities that are correlated to the target property.

In some embodiments, the process 104 of receiving an input includes loading calculated thermodynamic phase data, e.g., thermodynamic phase diagram data, from computer readable medium such as a storage device or a memory device. In some embodiments, the storage device or the memory device from which the input is received at the process 104 may be included within a material composition selection apparatus (FIG. 2) in the form of, for example, an internal storage device or an internal memory device, for instance a DRAM or an internal storage drive. In yet other embodiments, the input data may be received at the process 104 using a portable medium, such as a flash drive or an optical media such as a CD ROM. In other embodiments, the input data may be received at the process 104 via a network from a remote server, for example where the thermodynamic phase data may have been calculated. In yet other embodiments, the input data may be received at the process 104 via an input terminal such as a keyboard, an image sensor, a voice sensor and a scanner, among other input terminals through which a user can enter data.

In some embodiments, the process 116 of electronically mining does not include calculating additional thermodynamic phase data or extracting thermodynamic quantities therefrom after storing the extracted numerical quantities.

In some embodiments, the method 100 of selecting the composition does not include analysis of a graphical representation of the phase data.

In some embodiments, the method 100 further comprises synthesizing the material having a composition corresponding to one of the ranked materials.

In some embodiments, the process 108 of extracting comprises executing an algorithm to extract, for each material, the thermodynamic quantities selected from the group consisting of a mole fraction of a material phase at a temperature, a formation temperature of a material phase, a dissolution temperature of a material phase, a transition temperature between two phases, a weight percent of an element in a material phase at a temperature, a mole fraction of a first material phase at a temperature corresponding to a formation temperature or a dissolution temperature of a second phase and a weight percent of an element in a material phase at a temperature corresponding to a formation temperature or a dissolution temperature of a second phase. In some embodiments, the process 108 of extracting further comprises executing an algorithm to calculate a quantity derived from one or more of the thermodynamic quantities using a mathematical expression. The mathematical expression can be selected from the group consisting of a difference in formation temperature of two material phases, a difference in dissolution temperatures of two material phases, a sum of mole or weight fractions of at least two material phases at a temperature, a sum of mole fractions of at least two material phases at a temperature that are present at or below a second temperature.

In some embodiments, the process 116 of electronically mining comprises comparing at least a subset of the materials in parallel based on at least a subset of the thermodynamic quantities that are correlated to the target property.

In some embodiments, the process 116 of electronically mining comprises, before ranking the materials, initially eliminating from an entire set of the plurality of materials one or more material candidates based on one or more criteria selected from a minimum threshold thermodynamic quantity, a maximum threshold thermodynamic quantity and a range between a minimum threshold thermodynamic quantity and a maximum threshold thermodynamic quantity. In some embodiments, the process 116 of electronically mining comprises ranking the at least the subset of materials after eliminating from an entire set one or more material candidates.

In some embodiments, the entire method 100 is performed using a computer system. In other embodiments, only a subset of the method 100 can be performed using a computer. For example, predetermining the extracted thermodynamic quantities to be correlated to microstructures associated with physical properties of the material can be performed either using a computer system or performed by a skilled artisan.

In some embodiments, the method 100 is performed using a computer system comprising at least one microprocessor. In other embodiments, some features of the method are performed using a subset of the microprocessors of a computer system while other features of the method are performed using a different subset of microprocessors of the computer system.

In some embodiments, the method 100 further comprises outputting information regarding the ranking of the materials. In other implementations, the information is output to a display. In yet other implementations, the information is output to a computer-readable medium.

Figure 2:
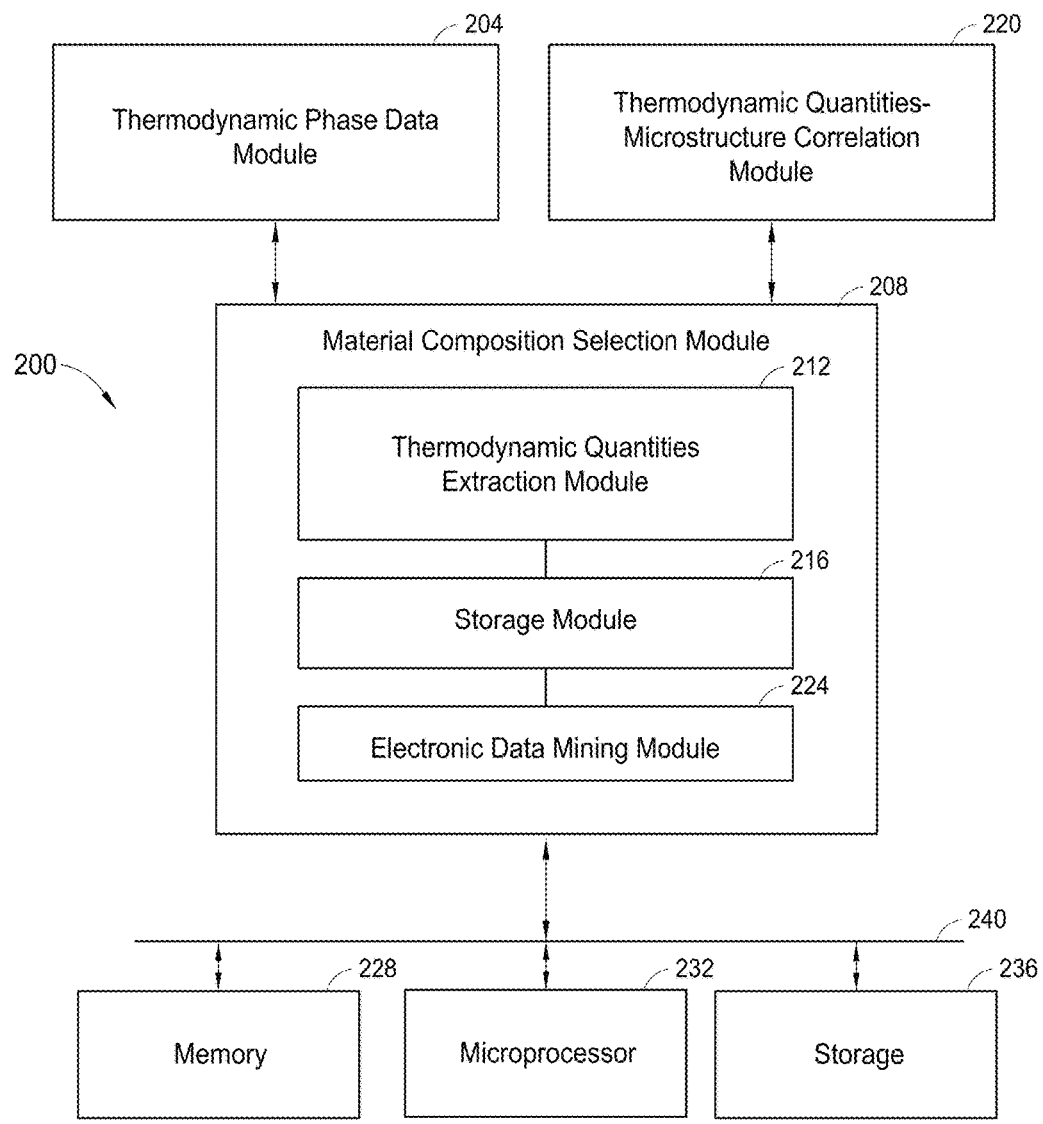
FIG. 2 is a schematic illustration of an apparatus for selecting a composition of a material having a target property, according to one embodiment.

FIG. 2 is a schematic illustration of an apparatus for selecting a composition of a material having a target property, according to one embodiment. The material composition selection apparatus 200 comprises a material composition selection module 208, a memory 228, a microprocessor 232, and a storage 236, which are communicatively coupled to each other via a bus 240. The memory 228 includes one or more volatile memory devices, such as, for example, a DRAM and/or an SRAM. The storage 236 includes one or more nonvolatile storage devices, such as magnetic hard drives and/or non-magnetic solid state drives, which can in turn include flash memory and/or other nonvolatile memory devices.

In the illustrated embodiment of FIG. 2, the material composition selection module 208 is also communicatively coupled to a thermodynamic phase data module 204 and a thermodynamic quantities-microstructure correlation module 220. The material composition selection module 208 includes a thermodynamic phase data extraction module 212 configured to receive an input comprising thermodynamic phase data from the thermodynamic phase data module 204, for a plurality of materials and configured to extract therefrom a plurality of thermodynamic quantities corresponding to each of the materials using the microprocessor 232. In the illustrated embodiment, the extracted thermodynamic quantities are predetermined by the thermodynamic quantities-microstructure correlation module 220 to have correlations to microstructures associated with physical properties of the material. The material composition selection module 208 additionally includes a storage module 216 configured to store the extracted numerical quantities in a computer-readable medium, which can be one or both of the memory 228 or the storage 236. The material composition selection module 208 further includes an electronic data mining module 224 configured to electronically mine the thermodynamic quantities stored by the storage module 216 using the microprocessor 232 to rank at least a subset of the materials based on a comparison of at least a subset of the thermodynamic quantities that are correlated to the target property. Each of the thermodynamic quantities extraction module 212, the storage module 216 and the electronic data module 224 includes specialized algorithms described in the following that are implemented on a hardware, which can be at least portions of the memory 228, microprocessor 232, and/or the storage 236. In some embodiments, at least portions of the algorithms of the thermodynamic quantities extraction module 212, the storage module 216 and the electronic data mining module 224 can be detached from the material composition selection apparatus 200 via a portable storage 236.

In the following, with respect to FIGS. 3, 4, 5A, 5B, 6A and 6B, by way of example and without losing generality, a concrete example of a method of selecting a composition of a material having a target property is illustrated.

Figure 3:
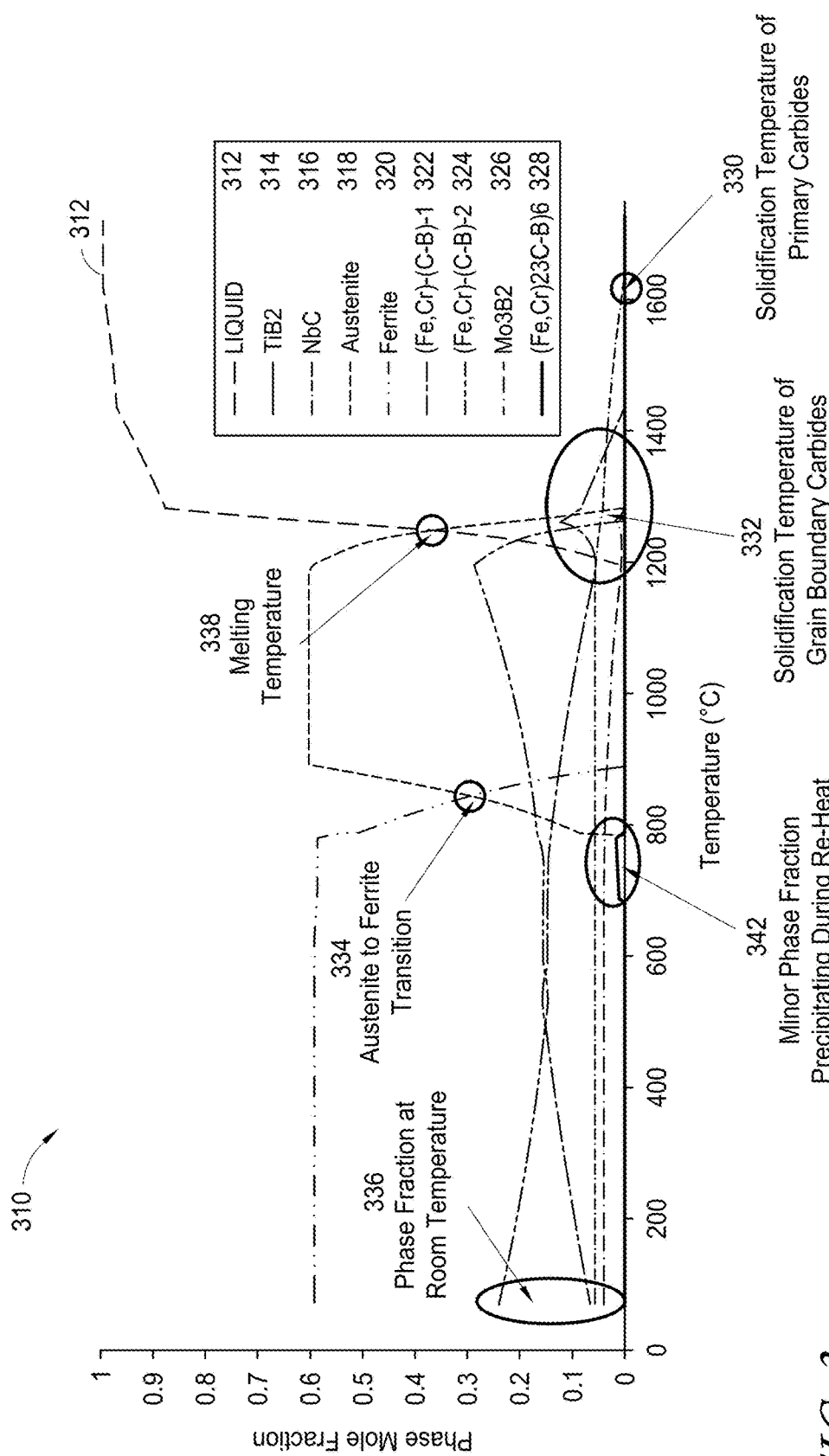
FIG. 3 illustrates a calculated phase diagram according to one embodiment.

FIG. 3 illustrates a calculated phase diagram according to one embodiment. In some embodiments, the method of selecting the composition includes receiving an input comprising thermodynamic phase data for a plurality of alloys where each alloy is a multi-phase system. In some embodiments, thermodynamic phase diagrams can be calculated using a suitable method, for example, using a method of Computer Calculations of Phase Diagrams (CALPHAD). In embodiments employing the CALPHAD method, a computer system uses a mathematical model to calculate Gibbs free energy curves of the individual phases of an alloy composition. For some phases of the material system, an analytical expression for calculating the Gibbs free energy may not exist. Therefore, the Gibbs free energy curves are calculated using the computer system by fitting mathematical models to experimental data using adjustable parameters. The adjustable parameters may be retrieved from a computer storage system. Subsequently, the Gibbs energy curves of the individual phases can be combined to describe a multi-phase alloy system. In some embodiments, the calculation of phase diagram using the CALPHAD method can be implemented in commercially available software packages such as Thermo-Calc (thermocalc.com/).

In some embodiments, a typical alloy system has at least four elements. The calculated phase diagram 310 is for an example composition of an Alloy System 1 having a composition (in wt. %) of $Fe_{bal}B_{1.3}C_{0.8}Cr_5Mn_1Mo_1Nb_4Si_{0.5}Ti_{0.5}V_{0.5}$. The phase diagram 310 displays equilibrium mole fractions of thermodynamically stable phases on the y axis as a function of temperature displayed on the x-axis. FIG. 3 includes mole fraction curves of stable phases of the composition of the Alloy System 1 including phases of liquid 312 and first through ninth phases that are, in the illustrated embodiment, $TiB_2$ 314, NbC 316, austenite 318, ferrite 320, (Fe,Cr)—(C,B)-1 322, (Fe,Cr)—(C,B)-2 324, $Mo_3B_2$ 326 and (Fe,Cr)23(C,B)6 328.

In some embodiments, a method of designing an alloy includes extracting from the phase diagrams thermodynamic quantities corresponding to each of the plurality of alloys, where the thermodynamic quantities comprise numerical quantities that correspond to properties of the alloys. In some embodiments, the thermodynamic quantities comprise single numerical quantities. In other embodiments, the thermodynamic quantities comprise quantities derived from the single numerical quantities using an algorithm.

Still referring to FIG. 3, in some embodiments, extracting the thermodynamic quantities comprises extracting a solidification temperature of at least one thermodynamically stable phase. For example, in FIG. 3, the solidification temperatures of thermodynamically stable phase includes a solidification temperature 330 of a primary carbide, which can include NbC, and solidification temperatures 332 of grain boundary carbides, which can include (Fe,Cr)—(C, B)-1, (Fe,Cr)—(C,B)-2, and (Fe,Cr)23(C,B)6.

Still referring to FIG. 3, in some embodiments, extracting the thermodynamic quantities comprises extracting a phase transition temperature from a first phase to a second phase. For example, in FIG. 3, extracting the thermodynamic quantities includes extracting a phase transition temperature 334 corresponding to a phase transition temperature from an austenite phase to a ferrite phase. While the phase transition temperature 334 in this example refers to a temperature at which percent mole fractions of austenite and ferrite phases are about equal, the phase transition temperature can be extracted anywhere from an overlapping region between the mole fraction curves of the austenite phase 318 and the ferrite 320, where a first rate of change of mole fraction of the ferrite phase 320 as a function of temperature is negative and a second rate of change of mole fraction of the austenite phase 318 as a function of temperature is positive. A rate of change can be represented for example by dc/dT, where dc is a change in percent of mole fraction of a phase and dT is a change in the temperature corresponding to the change in the percentage of mole fraction of the phase.

Still referring to FIG. 3, in some embodiments, extracting the thermodynamic quantities comprises extracting an equilibrium mole fraction of at least one thermodynamically stable phase at a specified temperature. For instance, in FIG. 3, equilibrium mole fractions 336 can include equilibrium mole fractions between a first temperature and a second temperature (about 0° C. and 100° C. in the illustrate embodiment) of liquid 312, $TiB_2$ 314, NbC 316, austenite 318, ferrite 320, (Fe,Cr)—(C,B)-1 322, (Fe,Cr)—(C,B)-2 324, $Mo_3B_2$ 326, and (Fe,Cr)23(C,B)6 328. In addition, a minor phase fraction 342 precipitating during re-heat can be extracted within a temperature range (between a third temperature and a fourth temperature of about 680° C. and 800° C., respectively, in the illustrated embodiment).

Still referring to FIG. 3, in some embodiments, extracting the thermodynamic quantities comprises extracting a melting temperature, wherein extracting the melting temperature includes extracting a temperature at which a first rate of change of mole fraction of at least one thermodynamically stable phase is negative and a second rate of change of mole fraction of a liquid phase as a function of temperature is positive. For example, while in FIG. 3, melting temperature 338 corresponds to a temperature at which the percent mole fractions of the liquid and austenite phases 312 and 318 are about equal, the melting temperature can be extracted anywhere within an overlapping region between the mole fraction curves of the liquid phase 312 and any other phase, in which a first rate of change of mole fraction of at least one thermodynamically stable phase is negative and a second rate of change of mole fraction of the liquid phase 312 as a function of temperature is positive.

In some embodiments, calculating a phase diagrams and extracting thermodynamic quantities from the phase diagram are run iteratively for each of the plurality of alloy compositions.

As an illustrative example, the extracted thermodynamic quantities may include: 1) phase fraction of NbC at 100° C., 2) solidification temperature of NbC, 3) solidification temperature of (Fe,Cr)—(C,B)-1, 4) solidification temperature of (Fe,Cr)—(C,B)-2, 5) phase fraction of (Fe,Cr)—(C,B)-1 at 100° C., and 6) phase fraction of (Fe,Cr)—(C,B)-2 at 100° C. The thermodynamic quantities may be iteratively extracted for the Alloy System 1 where the concentration of B is varied from 0.5 to 2.0 percent in steps of 0.5 percent, for a total of six alloys, and Ti is varied from 1 to 5 percent in steps of 0.5 percent, as an example.

In some embodiments, the method of selecting an alloy composition includes storing at least a subset of the numerical quantities extracted as described above in an electronic database. The numerical quantities that are stored represent a streamlined set of numerical quantities that are predetermined to have a correlation to certain microstructural properties. For example, the numerical quantities may be correlated to the presence of matrices and precipitates having specific phases of the alloy system. The microstructural properties can in turn be correlated to certain end material properties such as hardness, fracture toughness, magnetic permeability, etc.

The storage medium can include any suitable storage medium configured to store information with or without power supplied to the medium, including a volatile memory medium such as a DRAM and an SRAM, and/or a nonvolatile medium such as a flash memory or a disk drive. In some embodiments, the storage medium includes a removable storage media, such as a removable hard drive or a removable flash drive.

It will be appreciated that while it is possible to use techniques such as the CALPHAD method to calculate a phase diagram, a determination of which of the massive amount of information contained in the phase diagram are relevant in determining end material properties. For example, while the calculated phase diagram in FIG. 3 above shows a high fraction of high temperature forming NbC phase and no (Fe,Cr)—(C,B) phase, which forms above the austenite to ferrite transition temperature, the predetermination of these quantities as they relate to certain microstructural and material properties takes an understanding of experimental and theoretical physical metallurgy.

It will be appreciated that extracting thermodynamic quantities as described above can take a prohibitive amount of time and calculation resource without using the method described herein. For example, a single mole fraction curve of each stable phase in FIG. 3 comprises at least 30 individual data points. Without using a computer, it would take a person having ordinary skill in the art using a calculator, for example, at least several minutes per each data point. For an alloy having several phases such as in FIG. 3, calculation of mole fraction curves for all stable phases could take at least several hours. In order to calculate a system of alloys having several to several tens of compositions, extracting thermodynamic quantities can take days to weeks, if not longer. Using the methods described herein, similar calculations for an alloy system having several to several tens of compositions can be completed in several minutes to several hours. In some embodiments, over 1000 alloy compositions can be calculated in about two days.

The streamlined storage of predetermined numerical quantities as described above enables a fast retrieval of relevant information for a high throughput analysis. A typical analysis using the present method can be performed >1,000 times faster than conventional methods such as CALPHAD methods. This is because conventional methods utilize large thermodynamic databases, which utilize computationally expensive formulas to generate massive amounts of thermodynamic information. In contrast, the electronic database created in the present method is simply a series of numbers tied to alloy composition, which can be referenced, ranked, and used for alloy design in very short times.

An example set of stored numerical quantities is shown in the TABLE 1 that can be generated by the computing system. As noted above, it will be appreciated that while the values below may be inherently contained within a phase diagram, it takes a skilled metallurgist running a series of physical experiments (alloy manufacture, metallography, property measurement) to have predetermined that the numerical quantities have a correlation to certain material properties such as a desired microstructure that are in turn correlated to an end material property.

TABLE 1

| Alloy | Phase % NbC | NbC Solidfy T | Austenite Solidify T | FCC to BCC T | (Fe,Cr)-(C,B) Solidify T |
|---|---|---|---|---|---|
| 1 | 10 | 1600 | 1300 | 800 | 1200 |
| 2 | 5 | 1400 | 1350 | 950 | 1100 |
| 3 | 3 | 1500 | 1250 | 875 | 800 |
| 4 | 2 | 1100 | 1200 | 700 | 650 |

In some embodiments, the method of designing an alloy includes electronically mining the electronic database with a processor to rank the alloys based on a comparison of the numerical quantities for different alloy compositions. In some embodiments, the numerical quantities used to rank the alloys can be based on a subset of thermodynamic quantities that are extracted as described above. The mining process comprises referencing the specific thermodynamic quantities that have been predetermined to be correlated to useful microstructural and material properties as described above.

The described mining concept is an alloy design concept, which is separate and unique from utilizing a computer to execute thermodynamic calculations alone. In conventional CALPHAD techniques, the phase diagram is directly referenced by the metallurgist to understand alloy behavior. In this invention, the phase diagram is not referenced by the metallurgist, rather the user directly references the mined thermodynamic data for alloy design. This difference is unique and allows for one skilled in the art to evaluate the behavior of many alloys simultaneously and allows for one unskilled in the art to perform alloy design.

In some embodiments, electronically mining comprises ranking the alloys based on a subset of the numerical quantities stored in the electronic database. For example, referring back to TABLE 1, while all numerical quantities in TABLE 1 may be stored in a storage medium, a subset of the stored numerical quantities may be used for ranking the alloys. For example, the subset may include numerical quantities of Phase % NbC but exclude one or more of NbC solidification temperature (NbC solidify T), Austenite solidification temperature (Austenite Solidify T), FCC to BCC transition temperature (FCC to BCC T) and (Fe,Cr)—(C,B) solidification temperature ((Fe,Cr)—(C,B) Solidify T).

In some embodiments, electronically mining comprises ranking the alloys based on a comparison of solidification temperatures of at least two thermodynamically stable phases. For example, referring back to FIG. 3, alloys may be ranked based on a comparison between a solidification temperature 330 of a primary carbide (e.g., NbC) and a solidification of the austenite 318.

In some embodiments, electronically mining comprises ranking the alloys based on a comparison of a phase transition temperature from a first phase to a second phase against at a solidification temperature of a third phase. For example, referring back to FIG. 3, alloys may be ranked based on a comparison between the phase transition temperature 334 corresponding to a phase transition temperature from an austenite phase to a ferrite phase, and solidification temperature 332 of grain boundary carbides (e.g., (Fe,Cr)—(C,B)-1 322, (Fe,Cr)—(C,B)-2 324 and (Fe,Cr)23(C,B)6 328.

Figure 4:
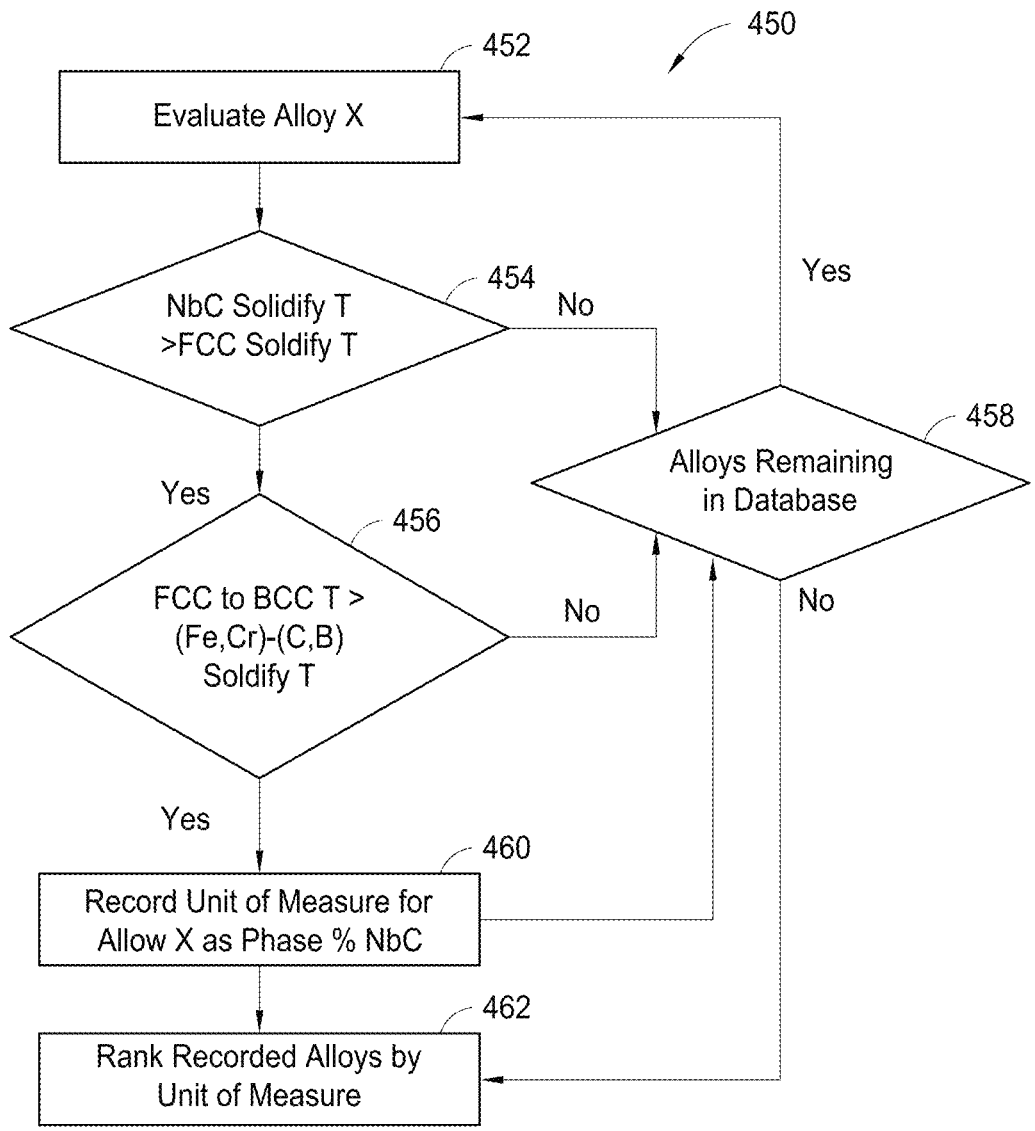
FIG. 4 is a flow chart illustrating a method of electronically mining as part of selecting a composition of a material having a target property, according to one embodiment.

FIG. 4 is a flow chart illustrating a method of electronically mining as part of selecting a composition of an alloy having a target property, according to one embodiment. The mining process 450 includes a process 452 of starting to evaluate an alloy. The process 452 can include retrieving, for example, a set of stored numerical quantities of an alloy composition as described above with respect to TABLE 1.

The mining process 450 additionally includes determining at a process 454 whether a solidification temperature of a first phase, e.g., an NbC phase, is greater than a solidification temperature of a second phase, e.g., an FCC phase.

Once the solidification temperature of the NbC phase is found to be greater than the solidification temperature of the FCC phase, the mining process proceeds to determining at a process 456 whether the a phase transition temperature from the FCC to a third phase, e.g., a BCC phase is greater than a solidification temperature of a fourth phase, e.g., a (Fe,Cr)—(C.B) phase.

On the other hand, if the solidification temperature of the NbC phase is found to be less than or equal to the solidification temperature of the FCC phase at the process 456, the mining process proceeds to determining at a process 458 whether there are additional alloys remaining in the database.

Once the phase transition temperature from the FCC to the BCC phase is determined to be greater than a solidification temperature of the (Fe,Cr)—(C.B) phase at the process 456, the data mining process 450 proceeds to a process 460 where a unit of measure for the alloy is recorded as a function of mole percent of the NbC phase. The unit of measure, for example, can be at least one of the NbC solidification temperature, the FCC solidification temperature, the phase transition temperature from the FCC to the BCC phase, and the solidification temperature of the (Fe,Cr)—(C.B) phase.

On the other hand, if the phase transition temperature from the FCC to the BCC phase is determined not to be greater than a solidification temperature of the (Fe,Cr)—(C.B) phase at the process 456, the mining process 450 proceeds to determining at a process 458 whether there are additional alloys remaining in the database.

At the process 458, if it is determined that additional alloys remain in the database to be evaluated, the mining process 450 starts another process 452 of starting to evaluate an additional alloy. On the other hand, at the process 458, if it is determined that no additional alloys remain in the database, the mining process 450 ranks the evaluated alloys according to the unit of measure.

In the foregoing, the method for designing an alloy was described in the context of calculation of equilibrium phase diagrams as a starting point and obtaining thermodynamic quantities therefrom. However, the embodiments described herein can apply to calculation of other calculations, including: calculations of chemical driving forces, CVD/PVD deposition simulations, CVM calculations of ordering/disordering phenomena, Scheil-Gulliver solidification simulations, liquidus and solidus surface projections, Pourbaix diagrams, Ellingham diagrams, partition coefficients, and partial gas pressures, among other calculations.

Figure 5A:
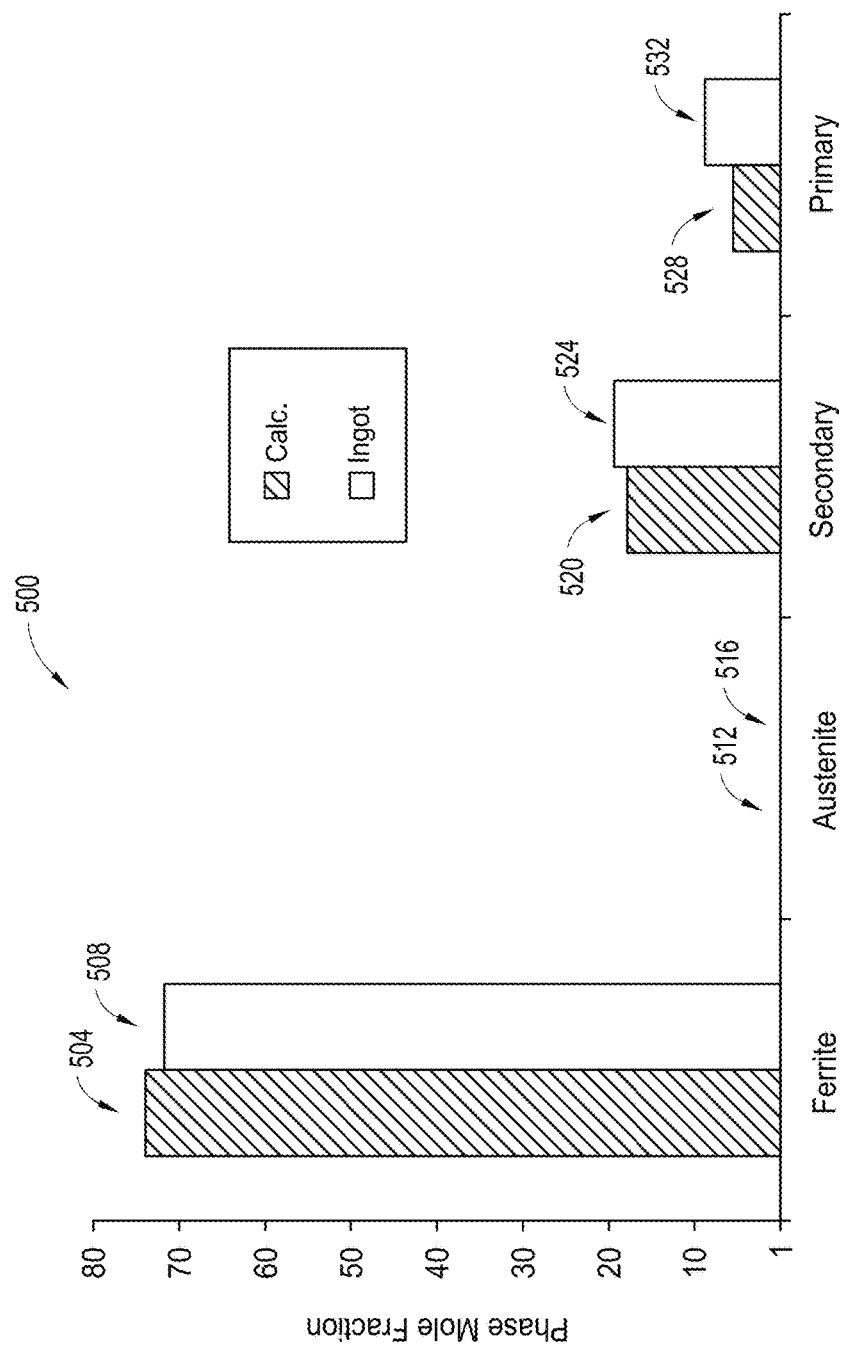
FIG. 5A is a chart illustrating a comparison between extracted thermodynamic quantities (calculated phase mole fractions) of a material and measured thermodynamic quantities (measured phase mole fractions) the material that are correlated to microstructures associated with a physical property of the material.
Figure 5B:
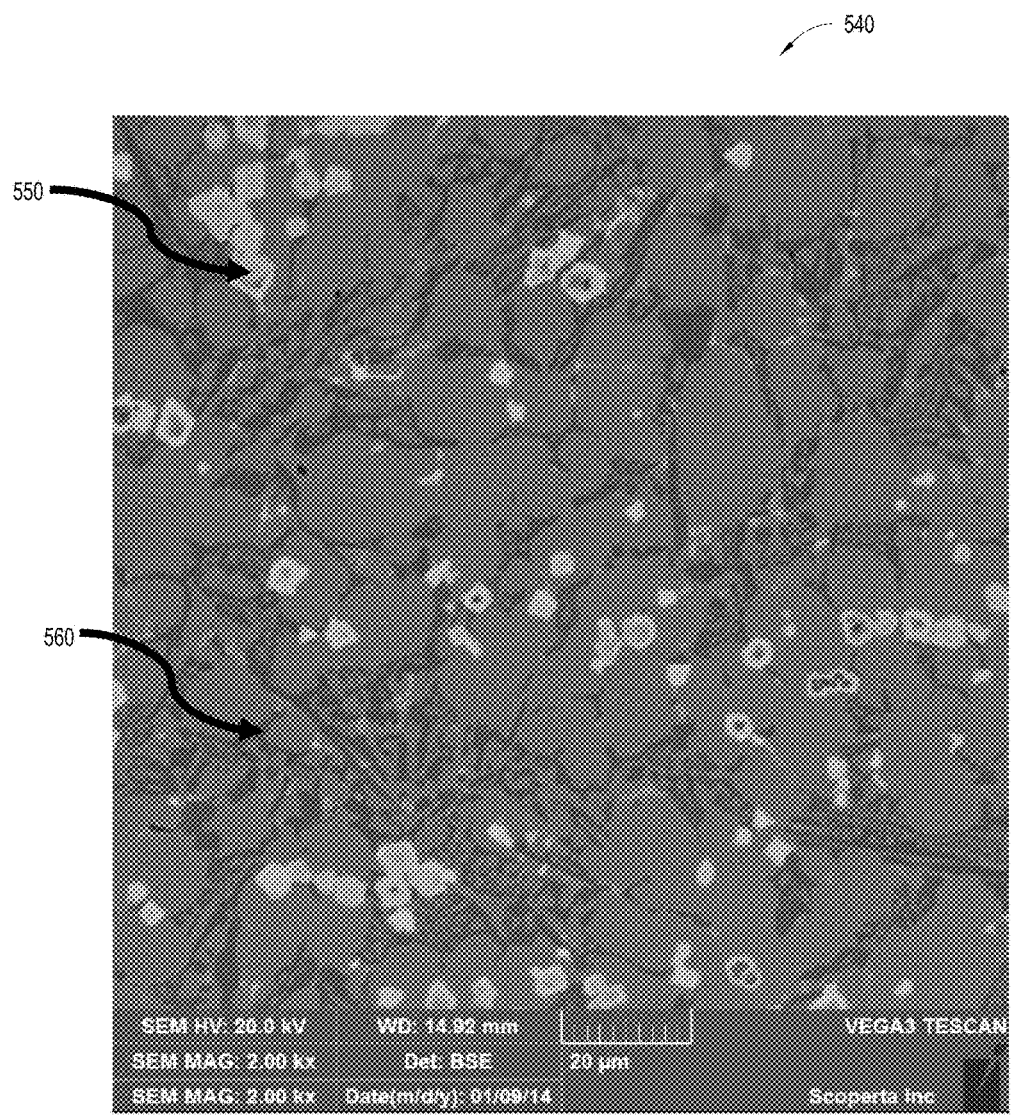
FIG. 5B is a scanning electron micrograph showing the microstructures of the material associated with the physical property of the material that was used to measure the thermodynamic quantities (measured phase mole fractions) plotted in FIG. 5A.

FIGS. 5A and 5B illustrate, by way of example and without loss of generality, correlating the extracted thermodynamic quantities of a material to microstructures associated with a target physical property of the material. FIG. 5A is a comparison bar graph 500 comparing extracted thermodynamic quantities (calculated phase mole fractions) 504, 512, 520, 528 of a material and measured thermodynamic quantities (measured phase mole fractions from an ingot) 508, 516, 524 and 532 that are correlated to microstructures associated with a physical property of the material. FIG. 5B is a scanning electron (SEM) micrograph 540 showing the microstructures of the material associated with the physical property of the material that was used to obtain the measured the thermodynamic quantities in FIG. 5A. The comparison bar graph 500 is that of a particular alloy $FeB_{1.4}C_{0.8}Cr_5Mo_1Nb_4Ti_{0.5}V_{0.5}$, and compares the calculated phase mole fractions 504, 512, 520 and 528 of ferrite, austenite, a secondary carbide and a primary carbide, respectively, against respective measured phase mole fractions 508, 516, 524 and 532 of ferrite, austenite, a secondary carbide and a primary carbide, respectively. The phase mole fractions for the illustrated example were obtained by analyzing the SEM micrograph 540 of FIG. 5B. Microstructural regions 550 and 560 of the SEM micrograph 540 correspond to the primary and secondary phases, in the illustrated example. It will be appreciated that the calculated and measure amounts of phase mole fraction are not the same, and an offset relationship can be a factor that is taken into consideration at a later mining stage. In the illustrated example, the inventors determined that the target properties of simultaneous high crack resistance and high wear resistance are correlated to the measured phase mole fractions 524 and 532 of the secondary carbide and the primary carbide, respectively. Furthermore, the microstructural locations of these phases were also determined to be correlated to the target properties. Based on this microstructural knowledge of the correlations between the thermodynamic quantities and the microstructures associated with the physical properties, the extracted thermodynamic phase data can later be mined for the specific physical properties. These advantages are described in more detail with respect to EXAMPLE 2, described below.

Figure 6A:
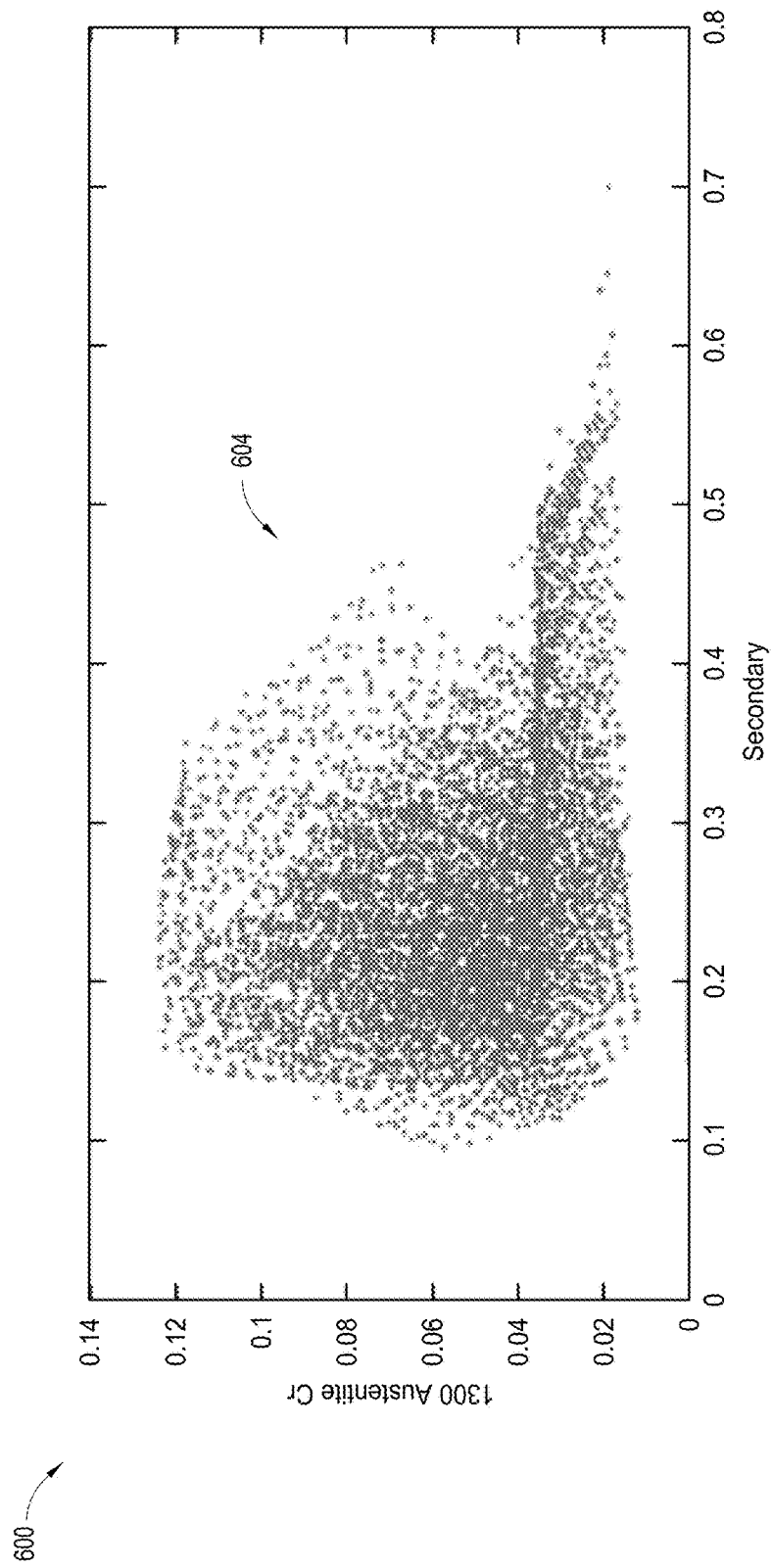
FIG. 6A is a chart illustrating an example of the data mining process involving 15,000 alloys, according to one embodiment.

FIG. 6A is a chart 600 illustrating an example of the electronic data mining process involving extracted thermodynamic quantities 604 of 15,000 alloys, according to an embodiment. The y axis represents a first thermodynamic quantity associated with a Cr content level in the austenite phase, and the x axis represents a second thermodynamic quantity associated with a secondary carbide content level. Based on a correlation between the thermodynamic quantities and microstructures associated with a target property in a similar manner as described above with respect to FIGS. 5A and 5B, the data base containing the extracted thermodynamic quantities can be mined for a specific combination of first and second thermodynamic quantities. Additional description of this process is provided below with respect to EXAMPLE 3.

Figure 6B:
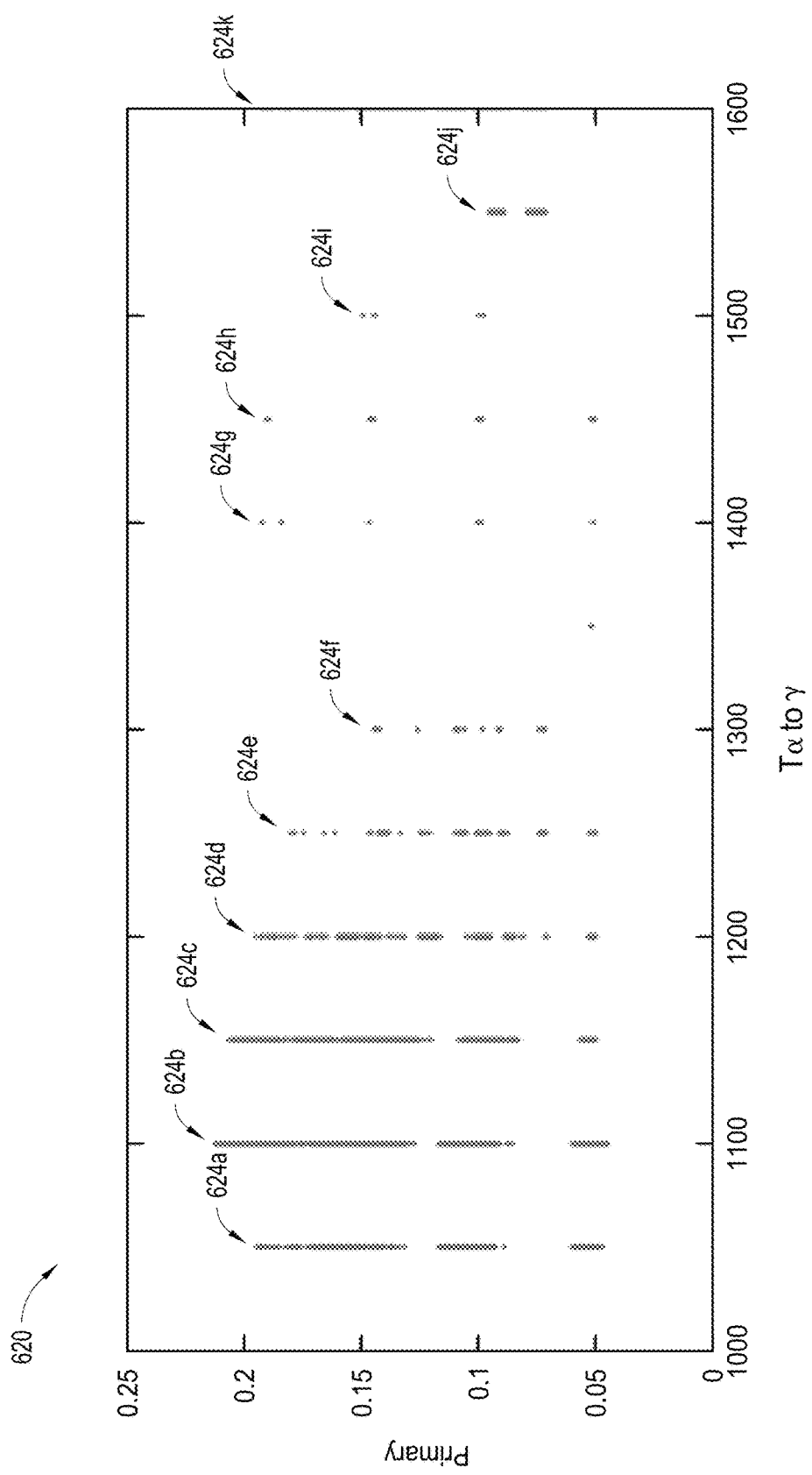
FIG. 6B is a chart illustrating another example of the data mining process involving 15,000 alloys, according to one embodiment.

FIG. 6B is a chart 620 illustrating another example of the electronic data mining process involving extracted thermodynamic quantities 624a-624k of 15,000 alloys, according to an embodiment. The x axis represents a first thermodynamic quantity associated with an FCC—BCC phase transition, and the y axis represents a second thermodynamic quantity associated with a primary carbide content level. Based on a correlation between the thermodynamic quantities and microstructures associated with a target property in a similar manner as described above with respect to FIGS. 5A and 5B, the data base containing the extracted thermodynamic quantities can be mined for a specific combination of first and second thermodynamic quantities. Additional description of this process is provided below with respect to EXAMPLE 3.

It will be appreciated that the results of both FIG. 6A and FIG. 6B can be obtained after the extraction process with no additional thermodynamic quantities extraction and no additional calculation of phase data. That is, a single data extraction process can be sufficient for multiple mining processes to determine material compositions for a variety of different target properties, which can be entirely independent of one another.

As discussed above, the method of designing an alloy according to embodiments herein are best implemented using an electronically implemented system including a processor comprising logic circuitry. FIGS. 7-10 illustrate embodiments of algorithms that can be executed on the system.

Figure 7:
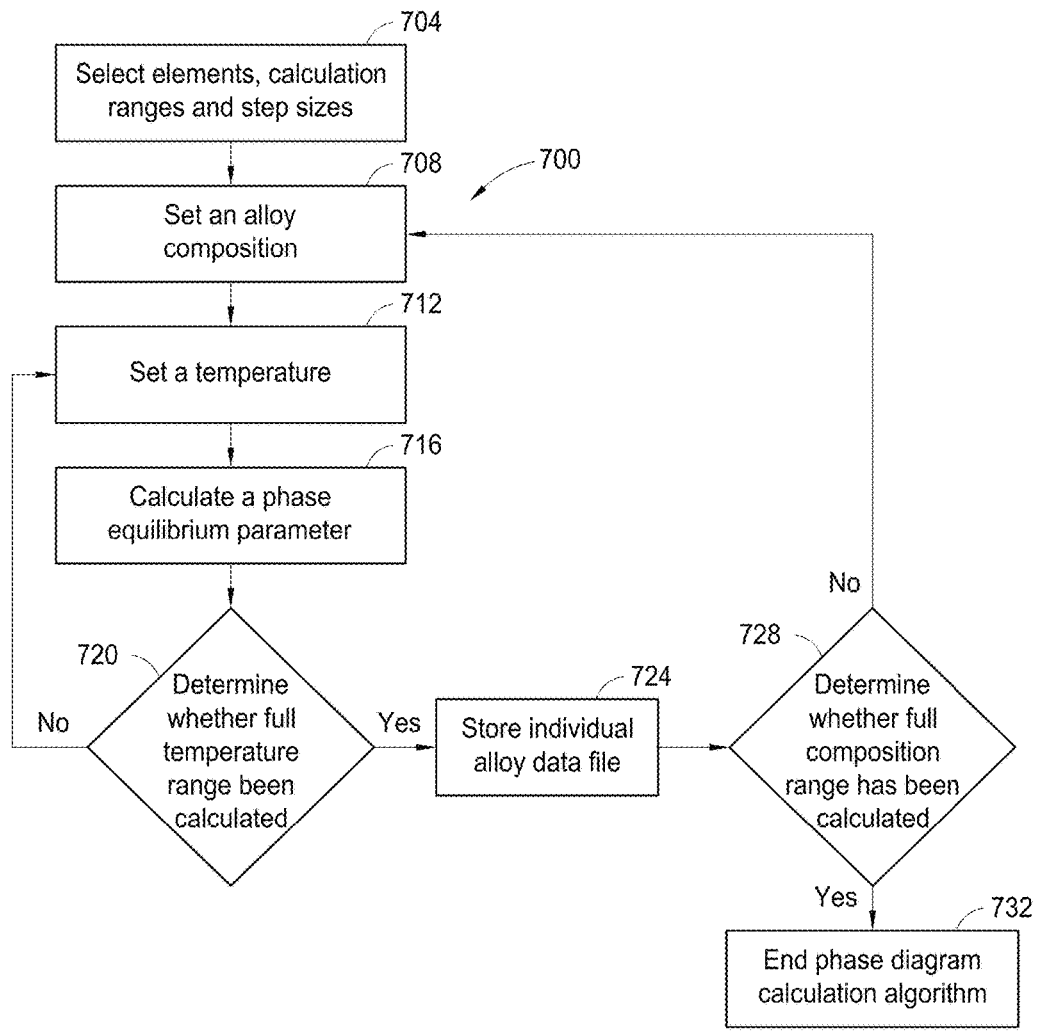
FIG. 7 is a flow chart illustrating a method of calculating a phase diagram according to one embodiment.
Figure 8:
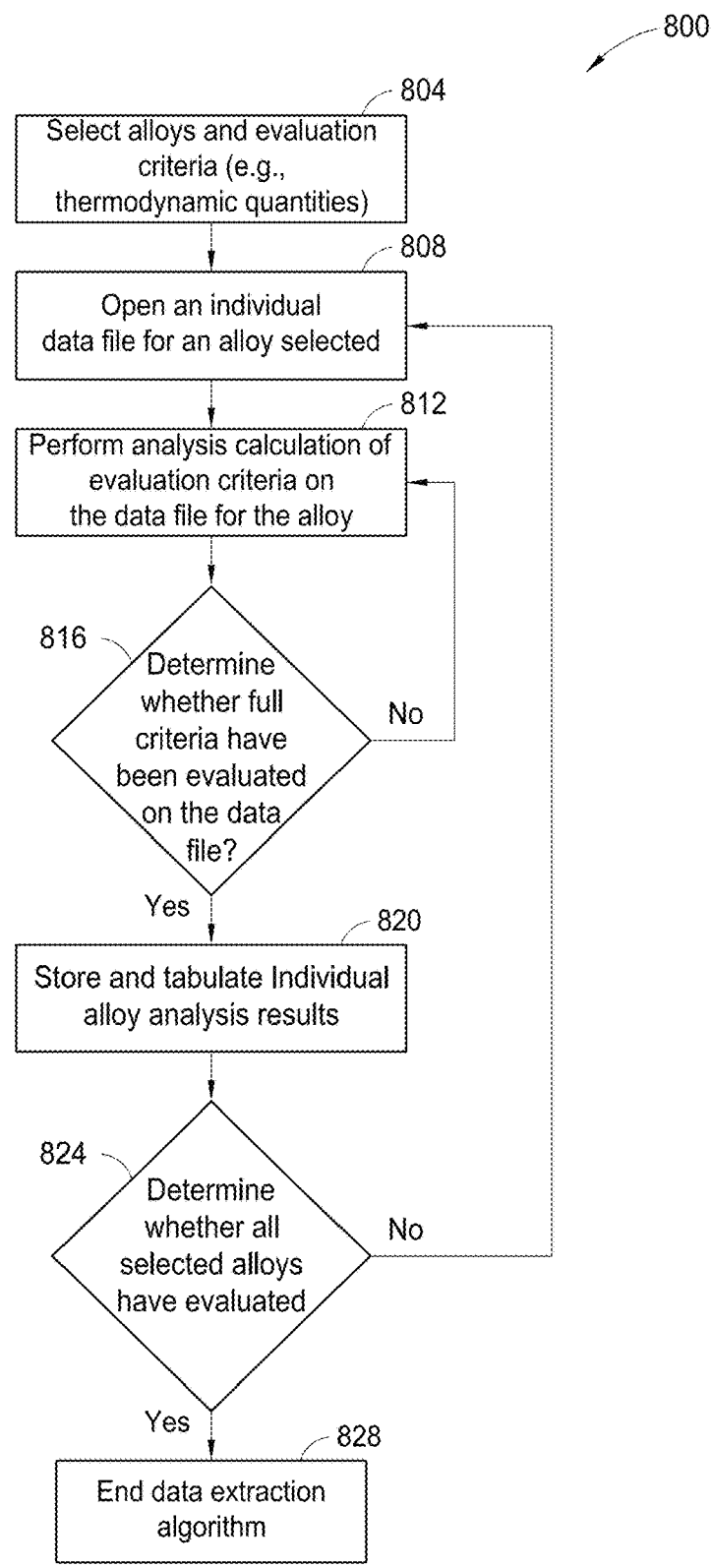
FIG. 8 is a flow chart illustrating a method of extracting from the phase diagram thermodynamic quantifies as part of selecting a composition of a material, according to one embodiment.
Figure 9:
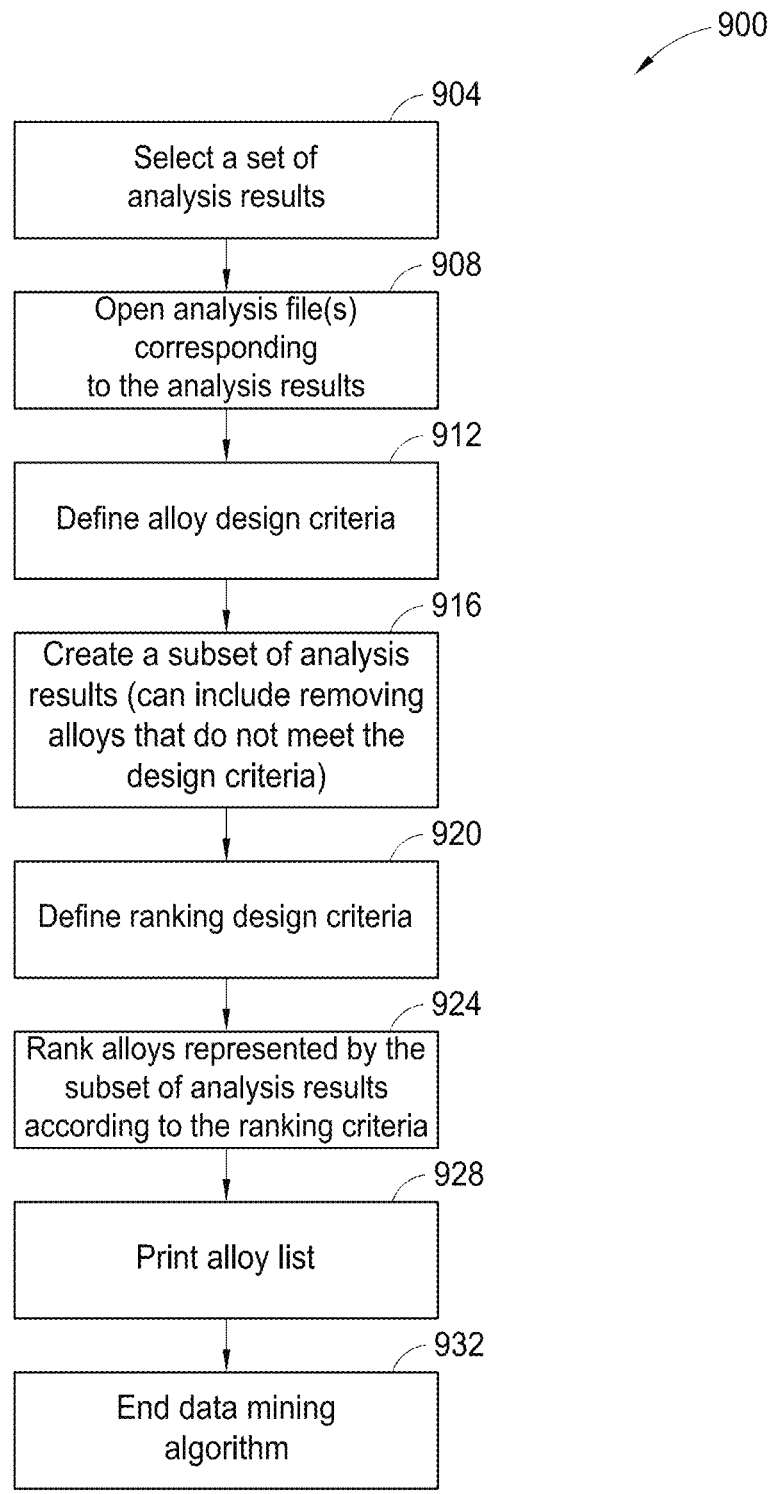
FIG. 9 is a flow chart illustrating electronically mining a data base as part of selecting a composition of a material, according to one embodiment.

FIGS. 7-10 illustrate a method for designing a material, e.g., an alloy, having a target property, including calculating thermodynamic phase diagrams for a plurality of materials using a processor comprising logic circuitry (FIG. 7), extracting from the phase diagrams numerical thermodynamic quantities corresponding to each of the plurality of materials, wherein extracting is based on a set of predetermined thermodynamic evaluation criteria (FIG. 8), and electronically mining the stored numerical quantities with a processor to rank the materials based on a comparison of at least a subset of the numerical quantities for each material against a material design criteria corresponding to the target property (FIG. 9).

FIG. 7 is a flow chart illustrating a phase diagram calculation algorithm 100 for designing an alloy according to one embodiment, including calculating thermodynamic phase diagrams for a plurality of alloys using a processor comprising logic circuitry. In some embodiments, the algorithm depicted in FIG. 7 can be implemented as a stand-alone algorithm. In other embodiments, the algorithm 700 can be implemented as a subroutine, i.e., as part of a larger algorithm.

In the illustrated embodiment of FIG. 7, the phase diagram calculation algorithm 700 includes various processes including, at the beginning, a process 704 for selecting elements and specifying composition and/or temperature ranges and step sizes. For example, if carbon is specified as an element, a composition range from Min=0% to Max=1%, to be calculated at step increments of 0.1%, may be specified at the process 704. In addition, a temperature range from 300K to 2000K, for example, to be calculated at step increments of 50K, may be specified at the process 704.

Still referring to FIG. 7, the phase calculation algorithm 700 additionally includes a process 708 for setting an alloy composition. At the process 708, one alloy composition within the composition range specified in the process 704 may be set for calculation. For example, $Fe_{bal}B_{1.3}C_{0.8}Cr_5Mn_1Mo_1Nb_4Si_{0.5}Ti_{0.5}V_{0.5}$, may be a specific composition that can be set at the process 708 for setting the alloy composition. The phase diagram calculation algorithm 700 additionally includes a process 712 for setting a temperature within the temperature range specified in the process 704. For example, the first temperature to be calculated can be the minimum temperature value within the temperature range selected in the process 704.

Although not shown for clarity, in some embodiments, additional thermodynamic parameters may be set in addition to the temperature at the process 712, for example, to further reduce the degrees of freedom to zero. As used herein, the degree of freedom refers to the number of intensive properties such as temperature or pressure, which are independent of other intensive variables. The degree of freedom may be expressed, for example, by the Gibbs' phase rule, which states that $F=C-P+2$, where C is the number of components and P is the number of phases.

Still referring to FIG. 7, phase calculation algorithm 700 additionally includes calculating at a process 716 a phase equilibrium parameter or a set of phase equilibrium parameters, such as, for example, the mole fractions of the phases present at the temperature specified at the temperature setting process 712.

Still referring to FIG. 7, upon completion of the calculation of the phase equilibrium parameter at process 716, the phase calculation algorithm 700 proceeds to a decision process 720 to determine whether the phase equilibrium parameter last calculated at the process 716 corresponds to the last temperature of the full temperature range selected at the process 704. Upon determining at the process 720 that the calculation at the process 716 does not correspond to the last temperature of the range selected at the process 704, the algorithm 700 increments the temperature by a step size set at the process 704. For example, the temperature may be increased from 300 K to 350 K if the temperature step size is specified as 50 K at the process 704. The algorithm then loops back to the process 712 to calculate the next set of phase equilibrium parameters, e.g., mole fractions, at the newly set temperature value. The iterative loop continues until the full temperature range set at the process 704 has been calculated.

Still referring to FIG. 7, upon determination that the full temperature range has been calculated at the decision process 720, the phase diagram calculation algorithm 700 proceeds to store at a process 724, in an individual alloy data file, the calculated phase equilibrium parameters for the composition set at the process 708, for the full temperature range selected at the process 704. The stored alloy data may be in a tabulated form, for example, which can be stored as multiple spreadsheets with relevant thermodynamic information for an alloy design. For example, the first sheet may contain the mole fraction of each phase present in the alloy at all the calculated temperatures. Additional sheets may, for example, contain information such as the chemical composition of each present phase at all calculated temperatures.

Still referring to FIG. 7, after the individual alloy data file has been stored at the process 724, the phase diagram calculation algorithm 700 proceeds to determine at the decision process 728 whether the full range of the alloy composition specified at the process 704 has been calculated. Upon determination that the full range of the alloy composition has not been calculated, the algorithm 700 loops back to the process 708, where a new alloy composition is set and processes 708 to 724 are iteratively repeated until a determination is made at the decision process 728 that the full range of the alloy composition has been calculated. In some embodiments, the composition of one element can be varied for each loop from the process 708 to the process 728. In other embodiments, compositions of more than one (e.g., two or three) alloying elements can be varied for each loop. For example, after the full temperature range for an alloy has been calculated for a carbon content of 1 wt. %, the next alloy calculated can have a carbon content of 1.5 wt. % for a step size specified to be 0.5 wt. % carbon. The corresponding weight percent of the solvent element is thereby reduced by 0.5 wt. %, such that the composition of more than one alloying elements are varied for each loop. However, the algorithm can be designed to calculate more complex alloying variations if desired.

Still referring to FIG. 7, after the last individual alloy data file has been stored at the process 724 and a determination is made at the decision process 728 that the full range of the alloy composition has been calculated, the phase diagram calculation algorithm ends at the a process 732. In one example, upon completion of the phase diagram calculation algorithm 700, a data folder comprising individual files for each calculated alloy composition can be generated and stored.

It will be appreciated that in some embodiments, the phase diagram calculation algorithm 700 is automated such that the algorithm 700 is configured to take human input only at the process 704 for selecting elements and specifying calculation ranges and step sizes, such that the subsequent processes 708-732 can be performed, and the results stored, automatically for the entire set of elements over the entire calculation ranges specified at the process 704. It will be further appreciated that the amount of data obtained for a typical calculation is practically prohibitive to calculate or handle without an algorithm such as the algorithm 700 implemented in an electronically implemented system including a processor, as described herein. By way of an illustration only, an Fe-based alloy having the following elements can be considered: carbon (C), boron (B), titanium (Ti) and niobium (Nb). For example, the compositions for C and B can be selected to have a range between 0 and 1 wt. %, and the composition step size can be set at 0.1 wt. %. Additionally, the compositions for Nb and Ti can be selected to have a range between 0 and 10 wt. %, and the composition step size can be set at 1 wt. %. Additionally, the temperature can be selected to have a range between 300K and 2,000K, and the step size can be set at 50K. Such a range, which may be considered relatively coarse by a person having ordinary skill in the art for designing commercial alloys, can already yield a prohibitive amount of data for calculating and handling without an algorithm implemented in an electronic system including a microprocessor. To illustrate, calculation in this example would involve a data set including 11×11×11×11=14,641 different alloy compositions (i.e., 0-10 wt. % and 0-1 wt. % produces 11 different iterations with the given step sizes). In addition, for the specified temperature range and assuming a reasonable value of 5 phases present in each alloy, each alloy would contain 35×5 (phase mole fraction data)+5×4×35 (phase chemistry data)=875 data points per alloy composition. In sum, the entire sub-routine would have stored 14,641×875=10,248,875 data points, stored in 14,641 individual alloy data files.

Data extraction involves the compilation of relevant thermodynamic quantities from a phase diagram. The selection of this thermodynamic quantity must be executed by one skilled in the art of metallurgy, based on experimental measurements, for the purposes of predicting the microstructure and performance of calculated alloys. The thermodynamic quantities extracted from the phase diagram are not obviously present or apparent in the phase diagram itself. An additional calculation routine must be written and executed for each unique thermodynamic quantity of interest.

In one example the phase fraction is a desired thermodynamic quantity. As the phase fraction of each phase in a phase diagram changes and is thereby a function of temperature in addition to other variables, a skilled metallurgist must execute experimental trial in order to determine how to control these variables in order to extract the appropriate phase fraction as a numerical quantity for alloy design. In this and other examples, a separate algorithm must be written to extract the appropriate thermodynamic quantities.

In other examples, the thermodynamic quantities, which are extracted, are not present in the phase diagram at all, but rather are mathematical expressions of the information calculated from the information in the phase diagram. Similarly, a unique calculation routine must be written and executed to calculate and store a piece of numerical information, which is not present in the original phase diagram.

The above example illustrates that the extraction routine and the unique algorithms required to generate the thermodynamic quantities are not a mere rearrangement of the information present in the original phase diagram, rather it is the generation of new thermodynamic quantities which have additional benefit beyond the phase diagram alone in terms of executing alloy design.

The extraction step generates a new database which ties each alloy to each thermodynamic criteria. This database will act as the input for the data mining algorithms which is the actual stage of alloy design.

From the relatively vast amount of data, in the following, extracting a subset of thermodynamic quantities is described. FIG. 8 is a flow chart illustrating a data extraction algorithm 800 for designing an alloy according to one embodiment, including extracting from the phase diagrams numerical thermodynamic quantities corresponding to each of the plurality of materials, wherein extracting is based on a set of predetermined thermodynamic evaluation criteria, using a processor comprising logic circuitry. In some embodiments, the algorithm 800 depicted in FIG. 8 can be implemented as a stand-alone algorithm. In other embodiments, the algorithm 800 can be implemented as a subroutine, i.e., as part of a larger algorithm.

Still referring to FIG. 8, in some embodiments, the data extraction algorithm 800 can be configured to take as input the individual alloy data files created as a result of implementing the phase diagram calculation algorithm 800 of FIG. 8. The algorithm 800 includes various processes, including selecting alloys and evaluation criteria at process 804 at the beginning. In some embodiments, the process 804 may be performed manually, and may represent the only manual process among the processes included in the algorithm 800. The process 804 includes selecting one or more alloys, e.g., one or more alloys calculated in the phase diagram calculation algorithm 800 of FIG. 8. Furthermore, the process 804 includes specifying one or more evaluation criteria, which can be thermodynamic criteria by which the one or more alloys are to be evaluated. By way of an example, referring back to the example illustrated in TABLE 1, the five different criteria including phase % of NbC, NbC solidification temperature, austenite solidification temperature, FCC to BCC transition temperature, and (Fe,Cr)—(C, B) solidification temperature shown in TABLE 1 can represent the thermodynamic criteria selected at the process 804.

Still referring to FIG. 8, once the alloys and evaluation criteria are selected at the process 804, the algorithm 800 proceeds to open at a process 808 an individual data file corresponding to one of the individual alloys selected at process 804. Referring back to the Fe-based alloy example discussed in connection with FIG. 8 by way of illustration, the individual data file to be opened at process 808 may be one of the 14,641 individual alloy data files calculated as in executing the phase diagram calculation algorithm 700 in FIG. 7.

Still referring to FIG. 8, after opening the individual data file corresponding to the one of the individual alloys selected at process 808, the algorithm 800 proceeds to perform an analysis calculation at a process 812 on the individual data file for the alloy to evaluate the data file against the evaluation criteria (e.g., thermodynamic criteria) selected at the process 804. Referring back to the example of TABLE 1, the algorithm can, for example, scan the data points in the individual alloy file to determine parameters corresponding to each of the five thermodynamic criteria. The result of each analysis calculation may represent TABLE 1, for example.

Still referring to FIG. 8, after each performance at the process 812 of performing the analysis calculation, a determination is made at a decision process 816 as to determine whether all evaluation criteria have been evaluated for the individual data file. Upon determination that there are evaluation criteria remaining to be analyzed on the data file, the algorithm 800 loops back to the process 812 to perform additional analysis calculations on the data file iteratively until all evaluation criteria selected at the process 804 have been evaluated on the data file. Referring back to TABLE 1 by way of an example, the process loop between processes 812 and 816 continues until all five thermodynamic criteria listed in the first row of TABLE 1 have been calculated for the alloy represented by one of the rows.

Still referring to FIG. 8, once all evaluation criteria have been determined to have been evaluated at the decision process 816, the algorithm 800 proceeds to store the results of the calculation in a separate tabulated electronic file at a process 820. In one example, this can be in the form of a spreadsheet file. Referring back to the example of TABLE 1, the tabulated electronic file may be in a format similar to TABLE 1.

Once the results of the analysis calculations for an individual alloy has been tabulated and stored at the process 820, the algorithm 800 proceeds to a decision process of 824 to determine whether all of the alloys selected in the process 804 have been evaluated and their corresponding data stored. Upon determination that there are alloys remaining to be evaluated, the algorithm 800 loops back to the process 808 to open another individual alloy data file and performs the process loop from 808 to 820 continues until all alloys selected at process 804 have been evaluated, at which point the algorithm 800 proceeds to process 828 to end the data extraction algorithm 800.

Upon completion of the data extraction algorithm 800, a streamlined data set extracted from the initially much larger data set resulting from the phase diagram calculation algorithm 700 can be obtained and stored in a single streamlined data storage file, such as for example, a spreadsheet file similar in format to TABLE 1.

It will be appreciated that upon completion of the data extraction algorithm 800, the complex information contained within a phase diagram has been simplified into a set of discrete numerical quantities which can be further interpreted and evaluated using computational methods. For example, referring back to the previous example discussed in connection with FIG. 7 where 14,641 alloys have been calculated, implementation of the data extraction algorithm 800 on such data set streamlines vast amounts of thermodynamic information contained in 14,641 individual files to extract a single spread sheet summarizing the alloy compositions against key evaluation criteria. It will be further appreciated that while the calculation of all 14,641 alloys may take up to two weeks using a continuously running computer, the data storage step of the same quantity of alloys may take only several hours. The quantified information contained in this sheet can then be easily managed by a data mining algorithm, described below.

The mining method is an independent routine from the extraction method. For example, after one or more alloys have been calculated and this alloy set has been run through the extraction routine, multiple mining routines can be run using the extracted data without repeating the calculation or extraction steps again. Again, this marks a clear distinction between using a computer to execute the CALPHAD process. In this conventional method the computer is used to calculate phase diagrams, which a metallurgist can use for alloy design. Additional alloy design steps using computer based CALPHAD again requires additional calculations and/or evaluations of a phase diagram. In this invention, phase diagrams need not be calculated again for multiple design efforts and the metallurgist does not interface with the phase diagrams directly to execute alloy design. Rather he can continuously mine the newly developed database of thermodynamic quantities to design alloys. In this invention, the user can utilize the advantages of the computer based approach, but does not require additional calculations or interfacing with any phase diagrams for each unique alloy design concept.

The data mining steps enables another fundamental difference between traditional CALPHAD and computer assisted CALPHAD methods in that it enable alloy design without the use of a chart, plot, diagram or any display of thermodynamic information whereby one skilled in the art of metallurgy must interpret. The data mining stage executes alloy design through purely numeric and algorithmic evaluation. This method is beneficial for several reasons, 1) it is purely objective, no inherent knowledge of alloy behavior is required for design, 2) one who is not skilled in the art of metallurgy can execute alloy design based on a series of sorting and ranking steps.

For example, the extraction step may create a database of 100 alloys ties to 20 unique thermodynamic variables. At no stage is it necessary to plot the thermodynamic information into a visual or graphical format in order to execute alloy design. Rather, the thermodynamic parameters or a subset of those thermodynamic parameters can be used to sort and rank the alloys for the purposes of design.

FIG. 9 is a flow chart illustrating a data mining algorithm 900 for designing an alloy according to one embodiment, including electronically mining the stored numerical quantities with a processor to rank the materials based on a comparison of at least a subset of the numerical quantities for each material against a material design criteria corresponding to the target property. The data mining algorithm 900 can be implemented using a processor comprising logic circuitry. In some embodiments, the algorithm depicted in FIG. 9 can be implemented as a stand-alone algorithm. In other embodiments, the algorithm 900 can be a subroutine, i.e., part of a larger algorithm.

Referring to FIG. 9, in some embodiments, the data mining algorithm 900 can be configured to take as input the stored data resulting from the data extraction algorithm 800 of FIG. 8. In FIG. 9, the data mining algorithm 900 is initiated by selecting a set of analysis results to be mined at a process 904. For example, the streamlined data set extracted using the data extraction algorithm 800 can be selected at the process 904. After the set of analysis results are selected at process 904, analysis data files corresponding to the selected set of analysis results are opened at a process 908.

Still referring to FIG. 9, after opening the selected set of analysis results at the process 908, the data mining algorithm 900 proceeds to a process 912 for defining a set of design criteria to be applied to the set of analysis results selected at the process 904. The set of design criteria can include, in some embodiments, a plurality of thermodynamic criteria. For example, referring to the example of TABLE 1, the set of design criteria can include the phase equilibrium parameters (e.g., weight percentage of NbC) in the first row that are within predetermined target values. In other embodiments, the set of design criteria can also include economic criteria such as a cost per unit weight of the alloy composition represented by the analysis result.

Still referring to FIG. 9, the set of design criteria is then applied at a process 916 to create a subset of analysis results representing a subset of the original set of data analysis results selected at process 904. In some implementations, at the process 916, analysis results corresponding to alloys that do not meet the design criteria can be removed (i.e., electronically deleted) from the analysis results selected at the process 904 such that the removed alloys are no longer analyzed in subsequent processes of the data mining algorithm 900. In other implementations, at least some analysis results corresponding to alloy compositions that do not meet the design criteria are not removed/deleted, such that they remain within the subset of analysis results.

Still referring to FIG. 9, the data mining algorithm 900 additionally includes a process 920 for defining a set of ranking criteria to be applied to the subset of analysis results created in the process 912. The ranking criteria can be, for example, a set of criteria that may be weighted to generate an overall score based on the relative importance of each of the criteria. Based on the ranking criteria defined at the process 920, a ranked subset of analysis results can be generated at a process 924, whose results can be printed (electronically on a screen or a data file or physically on paper) at a process 928. An example of a print-out may include the printed ranked subset of analysis results in a form of a spread sheet whose rows are ordered in the order of decreasing score based on the weighted criteria. Another example of a print-out may additionally rank the columns in the order of the weight of each of the ranking criteria. For example, the first row of the spread sheet can list the highest ranked alloy having the highest overall score based on the weighted ranking criteria and the first column can represent the ranking criteria having the highest relative importance. Once the print-out is generated, the data mining algorithm ends at a process 932.

In some embodiments, the data mining algorithm 900 can be configured to be relatively open such that it can take additional input at various processes of the algorithm 900 in addition to the process 904 for selecting the set of analysis results. In these embodiments, a user can create new subroutines and mimic a skilled person trained in the art of metallurgy evaluating a series of individual phase diagrams for alloy design. Such a technique is not only useful in designing alloys in complex systems, but can also useful in understanding and determining relationships between thermodynamic criteria and actual alloy performance.

It will be appreciated that the amount of data obtained for a typical calculation is prohibitive to calculate and handle without employing the data mining algorithm 900 implemented in an electronically implemented system including a processor, as described herein. This can be illustrated using the example presented earlier in connection with the phase diagram calculation algorithm 700 (FIG. 7) where 14,641 alloys have been calculated and stored as individual data files, whose files have been further evaluated using the data extraction algorithm 800 (FIG. 8) to produce a single spreadsheet. In this example, the data mining sub routine opens and evaluates a single spreadsheet which contains 14,641×5 (5 different thermodynamic criteria)=73,205 data points. The computerized method described herein can open the single spreadsheet with 73,205 data point and perform the data mining algorithm 900 practically instantaneously, whereas without such a method, the processes can take hours to days.

Figure 10:
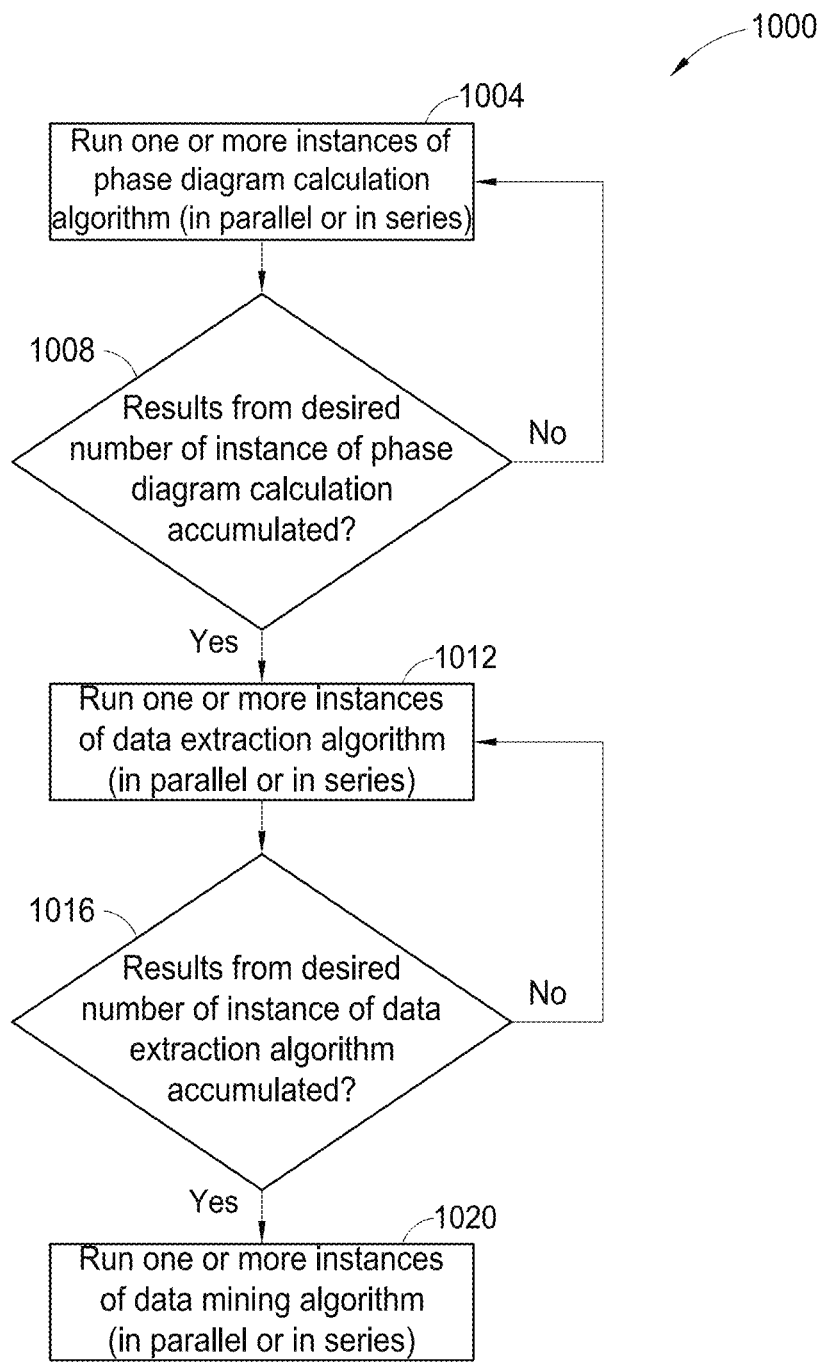
FIG. 10 is a flow chart illustrating a method of selecting a composition of a material, according to one embodiment.

It will be understood that the overall computation including executions of the phase diagram calculation algorithm 700 (FIG. 7), the data extraction algorithm 800 (FIG. 8), and the data mining algorithm (FIG. 9) can be managed such that a desired balance is struck between the overall speed of the computation and the available computational resources. FIG. 10 is a flow chart illustrating a method 1000 of managing the overall computation including executing the phase diagram calculation algorithm 700 (FIG. 7), the data extraction algorithm 800 (FIG. 8), and the data mining algorithm 900 (FIG. 9). The method 1000 includes a process 1004 of running one or more instances of the phase diagram calculation algorithm 700 (FIG. 7), either in series or in parallel. That is, one or more instances of the phase diagram calculation algorithm 700 can be run serially over a period of time on a single electronically implemented system, or alternatively, over a shorter period of time on a plurality of electronically implemented systems.

Subsequent to running the one or more instances of the phase diagram calculation algorithm 700 at the process 1004, the method 1000 proceeds to a decision process 1008 for determining whether or not results from a desired number of instances of phase diagram calculation algorithm 700 have accumulated. Upon determination at the decision process 1008 that the results from the desired number of instances have not accumulated, the method 1000 loops back to the process 1004 to run additional one or more instances of phase diagram calculation algorithm 700. On the other hand, upon determination at the decision process 1008 that the results from the desired number of instances have accumulated, the method 1000 proceeds to a process 1012 of running one or more instances of the data extraction algorithm 800 (FIG. 8), which can be run either in series or in parallel, similar to the process 1004.

Subsequent to running the one or more instances of the data extraction algorithm 800 at the process 1012, the method 1000 proceeds to a decision process 1016 for determining whether or not results from a desired number of instances of data extraction algorithm 1000 have accumulated. Upon determination at the decision process 1016 that the results from the desired number of instances have not accumulated, the method 1000 loops back to the process 1012 to run additional one or more instances of data extraction algorithm 800. On the other hand, upon determination at the decision process 1016 that the results from the desired number of instances have accumulated, the method 1000 proceeds to a process 1020 of running one or more instances of the data mining algorithm 900 (FIG. 9), which can be run either in series or in parallel, similar to processes 1004 and 1012.

Whether a particular algorithm is run in series or in parallel, and whether a particular algorithm will be run on results from a previous algorithm on a rolling basis or in a single instance can be determined based on the estimated computation resources for the algorithms such that the overall design of the alloy is optimized for the desired throughput based on the computational resources available.

In the following, an example implementation of the method of FIG. 10 is described for illustrative purposes. The initial set of alloy compositions to be calculated for one particular example may include, for example, 10,000 alloy compositions. Referring to FIG. 10, at process 1004, the phase diagram calculation algorithm 700 can set to be executed for the 10,000 compositions, for example, in 10 separate instances on 10 electronically implemented systems, where each electronically implemented system executes one instance of phase diagram calculation algorithm 700 for 1000 compositions, for example. The process loop 1004-1008 can be further configured to accumulate results from all 10 instances of the phase diagram calculation algorithm 700. After completion of each of the 10 instances from one of the ten electronically implemented system, the method 1000 determines at the decision process 1008 whether all 10 instances of the phase diagram calculation algorithm 700 have been run. Upon determining that less than all 10 instances have been run, the method 1000 loops back to the process 1004 to run additional instances of the phase diagram calculation algorithm 700 until all 10 instances have been executed, at which point the method 1000 proceeds to the process 1012 to run one or more instances of the data extraction algorithm 800. The results of the 10 instances executed in the process loop 1004-1008 can be organized, for example, as data structure including 10 folders, where each folder includes the results of one instance of the phase diagram calculation algorithm 700 from each electronically implemented system.

In the one particular example implementation of the method of FIG. 10, the results of all 10 instances of the phase diagram calculation algorithm 700 can be executed as a single instance of the data extraction algorithm 800. In addition, as an example, 700 different thermodynamic criteria may be selected to be evaluated (e.g., at process 804 in FIG. 8) for each of the results of phase diagram calculation algorithm 700 for the 10,000 alloy compositions. The output of the data extraction algorithm 800 can include, in this example, a spread sheet having 10,000 rows (e.g., 1 for each alloy) and 101 columns (e.g., 1 to specify each alloy and e.g., 100 to specify the 100 thermodynamic criteria). Of course, while in this example, only one instance of the data extraction algorithm 800 was specified to be run, if more than one instances of the data extraction algorithm 800 was specified to be run, the method 1000 determines at the decision process 1016 whether all specified instances of the data extraction algorithm 800 has been run, and if there are additional instances remaining to be run, the method 1000 loops back to the process 1012 to run the additional instances of the data extraction algorithm 800, until all specified instances have been run, at which point the method 1000 proceeds to a process 1020 to run one or more instances of the data mining algorithm 900.

In the one particular example implementation of the method of FIG. 10, the results of the one instance of the data extraction algorithm 800 can be executed at the process 1020 as multiple instances, in series or in parallel, of the data mining algorithm 900. For example, the multiple instances of the data mining algorithm 900 can represent ranking the 10,000 alloy compositions (e.g., at the process 924 in FIG. 9), for designing non-magnetic alloys, crack resistant hardfacing alloys, and corrosion resistant alloys.

It will be appreciated that, by the method described in FIG. 10 and the example implementation thereof, once the results from the 1012-1016 process loop (e.g., the spreadsheet with 10,000 columns and 101 rows in this example) is generated, it can used to design multiple types of alloys for different purposes (e.g., non-magnetic alloys, crack resistant hardfacing alloys, and corrosion resistant alloys), by simply executing subsequent instances of the data mining algorithm 900 (FIG. 9) at the process 1020 (FIG. 10) without having to repeatedly execute the phase diagram calculation algorithm 700 and the data extraction algorithm 800.

EXAMPLES

Example 1: Selecting a Non-magnetic Hardbanding Alloy Composition

This example details an alloy design routine that can be used to develop alloy compositions which are both non-magnetic and possess a high wear resistance and hardness. Such properties are not inherently contained in Fe-based materials, as the non-magnetic form of austenite is the softest form of iron. Thus, this challenging dual property material is a good candidate for demonstrating the capability of the described design concept, to illustrate the thorough investigation involved in the design of complex multi-component alloy systems. It was determined using a separate inventive process involving a comparison of experimentation and modeling results by one skilled in the art that the FCC—BCC transition temperature and the total hard particle phase fraction at 1300K were two thermodynamic criteria that can be used advantageously for designing alloys in this application space. Furthermore, it was determined by this separate inventive process that having a minimum FCC—BCC transition temperature of 950 K and a minimum hard particle phase fraction of 20 mole % were also advantageous for ensuring that such alloys had a high probability of meeting the performance requirements of this application space.

It can be appreciated that development of the $T(\gamma \to \alpha)$ thermodynamic quantity required an experimental correlation process to define. It can be appreciated that it is not inherently obvious to suggest that the design of a non-magnetic hardbanding alloy composition for room temperature applications would involve selecting an alloy which a phase diagram would suggest is magnetic at room temperature. However, a FCC—BCC transition temperature above room temperature means that the magnetic phase (BCC) of iron is thermodynamically stable at room temperature. This example illustrates that the phase diagram itself does not obviously contain the information useful for alloy design, rather this method often leads to the creation of thermodynamic quantities which are non-obvious or even counter to conventional metallurgical assumptions.

TABLE 2 represents the results of 11 instances of a phase diagram calculation algorithm similar to the phase diagram calculation algorithm 700 of FIG. 7. A description of the parameters used to run these sub-routines is shown in TABLE 2, including the minimum calculation range (min), maximum calculation (range), and step size (step) are shown for each element as well as the temperature. In each calculation series there are some elements which are held constant (at set values) throughout the sub-routine. The 11 instances of the phase diagram calculation algorithm generated 4,408 individual alloy data files.

TABLE 2

| Series No. | | B | C | Cr | Mn | Nb | Ni | Ti | V | W | Fe | Temp |
|---|---|---|---|---|---|---|---|---|---|---|---|---|
| 1 | Set | 1 | | | 10 | 4 | | 0.2 | 0.5 | 5 | Bal | |
| | Min | | 1.5 | 2 | | | 0 | | | | | 200 |
| | Max | | 3 | 18 | | | 10 | | | | | 2000 |
| | Step | | 0.5 | 2 | | | 2 | | | | | 50 |
| 2 | Set | 1 | | | 10 | 4 | | 0.2 | 0.5 | 5 | Bal | |
| | Min | | 1.5 | 2 | | | 0 | | | | | 200 |
| | Max | | 3 | 18 | | | 10 | | | | | 2000 |
| | Step | | 0.5 | 2 | | | 2 | | | | | 50 |
| 3 | Set | | | 18 | 5 | | 10 | 0.2 | 0.5 | | Bal | |
| | Min | 0 | 0 | | | 0 | | | | 1 | | 200 |
| | Max | 1 | 2 | | | 4 | | | | 5 | | 2000 |
| | Step | 0.2 | 2 | | | 2 | | | | 1 | | 50 |
| 4 | Set | 1 | | 18 | | | 10 | 0.2 | 0.5 | 5 | Bal | |
| | Min | | 0 | | 0 | 0 | | | | | | 200 |
| | Max | | 2 | | 10 | 4 | | | | | | 2000 |
| | Step | | 0.5 | | 1 | 1 | | | | | | 50 |
| 5 | Set | | | 18 | 5 | | 10 | 0.2 | 0.5 | | Bal | |
| | Min | 0 | 0 | | | 0 | | | | 1 | | 200 |
| | Max | 1 | 2 | | | 4 | | | | 5 | | 2000 |
| | Step | 0.2 | 2 | | | 2 | | | | 1 | | 50 |
| 6 | Set | | | | | | | 0.2 | 0.5 | | Bal | |
| | Min | 0 | 0 | 0 | 0 | 0 | | | | 0 | | 200 |
| | Max | 3 | | 20 | 10 | 4 | 10 | | | 4 | | 2000 |
| | Step | 0.75 | 10 | 5 | 2 | 5 | | | | 2 | | 50 |
| 7 | Set | 3 | | | 10 | | | 0.2 | 0.5 | | Bal | |
| | Min | | 10 | | | 0 | 0 | | | 0 | | 200 |
| | Max | | 20 | | | 4 | 10 | | | 4 | | 2000 |
| | Step | | 10 | | | 2 | 5 | | | 2 | | 50 |
| 8 | Set | 3 | | | | | | 0.2 | 0.5 | | Bal | |
| | Min | | 10 | 0 | 0 | 0 | | | | 0 | | 200 |
| | Max | | 20 | 5 | 4 | 10 | | | | 4 | | 2000 |
| | Step | | 10 | 5 | 2 | 5 | | | | 2 | | 50 |
| 9 | Set | 1 | | 18 | 10 | 4 | | | | | Bal | |
| | Min | | | | | | 0 | 0 | 0 | | | 200 |
| | Max | | | | | | 6 | 6 | 4 | | | 2000 |
| | Step | | | | | | 2 | 2 | 2 | | | 50 |

TABLE 2-continued

| Series No. | | B | C | Cr | Mn | Nb | Ni | Ti | V | W | Fe | Temp |
|---|---|---|---|---|---|---|---|---|---|---|---|---|
| 10 | Set | | | 18 | 10 | 4 | | | | | Bal | |
| | Min | 0 | 1.5 | | | | | 0 | 0 | 0 | | 200 |
| | Max | 1 | 3 | | | | | 6 | 6 | 4 | | 2000 |
| | Step | 0.5 | 0.5 | | | | | 2 | 2 | 2 | | 50 |
| 11 | Set | 1 | | 6 | 4 | | | 0.2 | 0.5 | | Bal | |
| | Min | | 1.5 | | | 0 | 4 | | | 5 | | 200 |
| | Max | | 3 | | | 4 | 10 | | | 15 | | 2000 |
| | Step | | 0.5 | | | 2 | 2 | | | 5 | | 50 |

Subsequently, a data extraction algorithm similar to the data extraction algorithm 800 of FIG. 8 was applied the results of the phase diagram calculation algorithm shown in TABLE 2. The data extraction algorithm was executed on all 4,408 alloy compositions initially calculated in the multiple instances of phase diagram calculation algorithm. The individual alloy data files were evaluated for the following thermodynamic criteria: (1) FCC—BCC transition temperature as defined by the highest temperature at which BCC Fe exists as a non-zero quantity; and (2) hard particle phase fraction at 1300 K as defined by the mole phase fraction sum of any carbides, borides, or intermetallics present at 1300 K in the alloy at equilibrium. At the conclusion of the data extraction algorithm, a single data file was generated tabulating the FCC—BCC transition temperature and hard particle phase fraction for each of the 4,408 alloy compositions.

Subsequently, a data mining algorithm similar to the data mining algorithm 900 of FIG. 9 was applied to the result of the data extraction algorithm described above. As mentioned, based on a separate inventive process it was determined that that a minimum FCC—BCC transition temperature ($T_{\gamma \to \alpha}$) of 950 K and a minimum hard particle phase fraction ($\Sigma_{hard}$) of 20 mole % were advantageous criteria for ensuring that such alloys had a high probability of meeting the performance requirements of this application space. Thus, two required design criteria were defined: ($T_{\gamma \to \alpha}$)>950 K and ($\Sigma_{hard}$)>20 mol %. Based on this filter, 643 alloys remained within the preferred design subset. Next, a ranking design criteria was defined: alloys were ranking according to ($\Sigma_{hard}$) with higher hard particle phase fractions being considered more favorable.

TABLE 3 represents a portion of an example of a final output of the data mining algorithm in a single table format having alloy compositions that are likely to be non-magnetic and possess a high hardness and wear resistance. Alloys are further organized in the data file according to the level of probable hardness and wear resistance. The alloy compositions listed in TABLE 3 represent those that are likely to be the hardest and most wear resistant alloys of the preferred subset:

TABLE 3

| Fe | B | C | Cr | Mn | Nb | Ni | Ti | V | W | $T_{\gamma \to \alpha}$ | $\Sigma_{hard}$ |
|---|---|---|---|---|---|---|---|---|---|---|---|
| 60.5 | 1 | 2.5 | 18 | 10 | 4 | 0 | 0 | 0 | 4 | 950 | 52% |
| 74.3 | 1 | 3 | 6 | 4 | 0 | 6 | 0.2 | 0.5 | 5 | 950 | 52% |

TABLE 3-continued

| Fe | B | C | Cr | Mn | Nb | Ni | Ti | V | W | $T_{\gamma \to \alpha}$ | $\Sigma_{hard}$ |
|---|---|---|---|---|---|---|---|---|---|---|---|
| 72.3 | 1 | 3 | 6 | 4 | 0 | 8 | 0.2 | 0.5 | 5 | 900 | 52% |
| 76.3 | 1 | 3 | 6 | 4 | 0 | 4 | 0.2 | 0.5 | 5 | 950 | 51% |
| 71.3 | 1 | 3 | 6 | 4 | 0 | 4 | 0.2 | 0.5 | 10 | 950 | 51% |

TABLE 3 demonstrates a small example of the ability to design an alloy without the need for one skilled in the art to evaluate thermodynamic information. This is an example of a table which simply links alloy compositions to two thermodynamic quantities. Such a table can contain a large number of unique alloys and a large number of unique thermodynamic quantities. Alloy design is then executed utilizing purely algorithmic sorting and ranking methods. In the above example the alloy at the top of the chart $Fe_{60.5}B_1C_{2.5}Cr_{18}Mn_{10}Nb_4W_4$ is the output of the full alloy design process, and is simply an alloy composition. The user did not need to evaluate phase diagrams or any graphical thermodynamic displays in order to identify this alloy. Furthermore, the user did not need to understand any correlation between alloy composition and desired performance, the algorithm simply identified the best candidate out of the dataset via purely objective numerical analysis.

Example 2: Selecting a Crack-resistant Hardfacing Alloy Composition

This example details an alloy design routine that can be used to develop alloy compositions which simultaneously have high wear resistance and are very resistant to cracking. Such properties are not inherently contained in Fe-based materials, as hardness and toughness (which provides resistance to cracking) are two properties known to those skilled in the art of metallurgy to be inversely related. Thus, this challenging dual property material is a good candidate for demonstrating the capability of the described design concept, to illustrate the thorough investigation involved in the design of complex multi-component alloy systems. It was determined using a separate inventive process involving a comparison of experimentation and modeling results by one skilled in the art that the total primary hard particle phase fraction and the total secondary hard particle phase fraction were two thermodynamic criteria that can be used advantageously for designing alloys in this application space. Furthermore, it was determined by this separate inventive process that a minimum primary hard particle phase fraction of 2 mole % and a maximum secondary hard particle phase fraction of 10 mole % were the required thresholds for ensuring that such alloys had a high probability of meeting the performance requirements of this application space.

TABLE 4 represents the results of 13 instances of a phase diagram calculation algorithm similar to the phase diagram calculation algorithm 700 of FIG. 7. A description of the parameters used to run these sub-routines is shown in TABLE 4, including the minimum calculation range (min), maximum calculation (range), and step size (step) are shown for each element as well as the temperature. In each calculation series there are some elements which are held constant (at set values) throughout the sub-routine. These 13 instances of the phase diagram calculation algorithm generated 9,132 individual alloy data files.

TABLE 4

| Series No. | | B | C | Cr | Mn | Mo | Nb | Si | Ti | Fe | Temp |
|---|---|---|---|---|---|---|---|---|---|---|---|
| 1 | Set | 0 | | 5.04 | 1.16 | 0.74 | | 0.76 | | Bal | |
| | Min | | 0.5 | | | | 0 | | 0 | | 200 |

TABLE 4-continued

| Series No. | | B | C | Cr | Mn | Mo | Nb | Si | Ti | Fe | Temp |
|---|---|---|---|---|---|---|---|---|---|---|---|
| | Max | | 2.5 | | | | 10 | | 10 | | 2000 |
| | Step | | 0.5 | | | | 2 | | 2 | | 50 |
| 2 | Set | | 1.07 | 5.04 | 1.16 | 0.74 | | 0.76 | | Bal | |
| | Min | 0 | | | | | 0 | | 0 | | 200 |
| | Max | 2 | | | | | 10 | | 10 | | 2000 |
| | Step | 0.5 | | | | | 2 | | 2 | | 50 |
| 3 | Set | | | 5.04 | 1.16 | 0.74 | | 0.76 | 3 | Bal | |
| | Min | 0 | 0 | | | | 0 | | | | 200 |
| | Max | 2 | 2.5 | | | | 10 | | | | 2000 |
| | Step | 0.5 | 0.5 | | | | 2 | | | | 50 |
| 4 | Set | | | | 1.16 | 0.74 | | 0.76 | 3 | Bal | |
| | Min | 0 | 3 | 0 | | | 4 | | | | 200 |
| | Max | 2 | 2.5 | 10 | | | 10 | | | | 2000 |
| | Step | 0.5 | 0.5 | 2 | | | 2 | | | | 50 |
| 5 | Set | | 2.5 | | 1.16 | 0.74 | | 0.76 | | Bal | |
| | Min | 0 | | 0 | | | 4 | | 0 | | 200 |
| | Max | 2 | | 4 | | | 10 | | 10 | | 2000 |
| | Step | 0.5 | | 2 | | | 2 | | 2 | | 50 |
| 6 | Set | | 2.5 | | 1.16 | 0.74 | | 0.76 | | Bal | |
| | Min | 0 | | 0 | | | 4 | | 0 | | 200 |
| | Max | 2 | | 4 | | | 10 | | 10 | | 2000 |
| | Step | 0.5 | | 2 | | | 1 | | 2 | | 50 |
| 7 | Set | | | | 1.16 | 0.74 | | 0.76 | | Bal | |
| | Min | | 2.5 | | | | 0 | | 0 | | 200 |
| | Max | | 5 | | | | 10 | | 10 | | 2000 |
| | Step | | 0.5 | | | | 2 | | 2 | | 50 |
| 8 | Set | | | 0 | 1.16 | 0.74 | | 0.76 | | Bal | |
| | Min | 0 | 1 | | | | 0 | | 0 | | 200 |
| | Max | 1.5 | 2.5 | | | | 5 | | 5 | | 2000 |
| | Step | 0.5 | 0.5 | | | | 1 | | 1 | | 50 |
| 9 | Set | | | 0 | 1.16 | 0.74 | | 0.76 | | Bal | |
| | Min | | 2.5 | | | | 4 | | 0 | | 200 |
| | Max | | 5 | | | | 10 | | 10 | | 2000 |
| | Step | | 0.5 | | | | 2 | | 1 | | 50 |
| 10 | Set | | | 0 | 1.16 | 0.74 | | 0.76 | | Bal | |
| | Min | 0 | 2.5 | | | | 4 | | 0 | | 200 |
| | Max | 2 | 5 | | | | 10 | | 10 | | 2000 |
| | Step | 0.5 | 0.5 | | | | 2 | | 2 | | 50 |
| 11 | Set | | | 0 | 1.16 | 0.74 | | 0.76 | | Bal | |
| | Min | | 0.8 | | | | 0 | | 0 | | 200 |
| | Max | | 1.6 | | | | 5 | | 5 | | 2000 |
| | Step | | 0.2 | | | | 1 | | 1 | | 50 |
| 12 | Set | | | 0 | 1.16 | 0.74 | | 0.76 | | Bal | |
| | Min | 0 | 0.8 | | | | 0 | | 0 | | 200 |
| | Max | 1 | 2.6 | | | | 5 | | 5 | | 2000 |
| | Step | 0.2 | 0.2 | | | | 1 | | 1 | | 50 |
| 13 | Set | | | 0 | 1.16 | 0.74 | | 0.76 | | Bal | |
| | Min | 0 | 0.8 | | | | 6 | | 6 | | 200 |
| | Max | 1 | 2.6 | | | | 10 | | 10 | | 2000 |
| | Step | 0.2 | 0.2 | | | | 1 | | 1 | | 50 |

Subsequently, a data extraction algorithm similar to the data extraction algorithm 800 of FIG. 8 was applied the results of the phase diagram calculation algorithm shown in TABLE 4. The data extraction algorithm was executed on all 9,132 alloy compositions initially calculated in the multiple data calculation sub-routines. The individual alloy data files were evaluated for the following thermodynamic criteria: (1) primary hard particle phase fraction as defined by the mole phase fraction sum at room temperature of any carbides, borides, or intermetallic phases which exist at a non-zero quantity at a temperature at least 10K above the highest temperature at which austenitic iron exists as a non-zero quantity; and (2) secondary hard particle phase fraction as defined by the mole phase fraction sum at room temperature of any carbides, borides, or intermetallic phases which exist at a non-zero quantity at a temperature less than 10K above the highest temperature at which austenitic iron exists as a non-zero quantity. At the conclusion of the data extraction algorithm, a single data file was generated tabulating these 2 thermodynamic quantities for each of the 9,132 alloy compositions.

Subsequently, a data mining algorithm similar to the data mining algorithm 900 of FIG. 9 was applied to the result of the data extraction algorithm described above. As mentioned, based on a separate inventive process it was determined that a minimum primary hard particle phase fraction (primary) of 2 mole % and a maximum secondary hard particle phase fraction (secondary) of 10 mole % were the required thresholds for ensuring that such alloys had a high probability of meeting the performance requirements of this application space. Thus, two required design criteria were defined: primary >2% and secondary <10 mol %. Based on this filter, 341 alloys remained within the preferred design subset. Next, a ranking design criteria was defined: alloys were ranking according to (Primary) with higher primary hard particle phase fractions being considered more favorable. TABLE 5 represents a portion of an example of a final output of the data mining algorithm.

TABLE 5

| Fe | B | C | Cr | Mn | Mo | Nb | Si | Ti | Primary | Secondary |
|---|---|---|---|---|---|---|---|---|---|---|
| 72.8 | 2 | 2.5 | 0 | 1.16 | 0.74 | 10 | 0.76 | 10 | 33.9% | 0.9% |
| 70.8 | 2 | 2.5 | 2 | 1.16 | 0.74 | 10 | 0.76 | 10 | 33.7% | 5.2% |
| 73.8 | 2 | 2.5 | 0 | 1.16 | 0.74 | 9 | 0.76 | 10 | 32.9% | 2.1% |
| 74.8 | 2 | 2.5 | 0 | 1.16 | 0.74 | 8 | 0.76 | 10 | 31.9% | 3.1% |
| 72.8 | 2 | 2.5 | 2 | 1.16 | 0.74 | 8 | 0.76 | 10 | 31.3% | 5.8% |

Example 2 is a good illustration of the extraction method and the necessity to have a special algorithm and calculation routine built to extract thermodynamic information from a phase diagram which is not inherently obvious or present in the thermodynamic phase diagram itself. In this example, primary and secondary hard particles are differentiated based on the formation temperature of the phases themselves in relationship to the formation temperature of the steel phase, austenite or ferrite. Given the number of potential hard phases that are potentially present when calculating 9,000 alloys, a relatively complex algorithm must be constructed to properly extract this information. In other words, the thermodynamic quantity labelled as 'Primary' is created using a sophisticated algorithm which interrogates a phase diagram, but ultimately is simply a number. The thermodynamic quantity labelled 'Secondary' is similarly extracted. These two example illustrate that the thermodynamic phase diagram is being utilized to create a separate and unique database which can be effectively mined at a later stage.

To illustrate the inherent complexity of the thermodynamic quantity 'Primary' a description of the algorithm to generate this number is provided. First, the algorithm determines whether austenite or ferrite is the Fe-based phase which is present at the highest temperature. The highest temperature at which either of these two phases is present is determined to be temperature 1. Second, the algorithm determines all of the other phases present over the temperature range of calculation. Thirdly, the formation temperature of each of the 'other phases' is determined and recorded. The formation temperature is defined as the highest temperature at which the specified phase has a non-zero mole fraction. Fourthly, the algorithm evaluates whether the formation temperature for each of the 'other phases' is greater than temperature 1. If the formation temperature is higher, the phase is regarded as a primary hard phase. If the formation temperature is lower, the phase is regarded as a secondary hard phase. Fifthly, the primary carbides mole fractions at a specified temperature of 300 K are summed up and extracted into a database under the column descriptor 'Primary'. It can be appreciated that the thermodynamic quantities are not merely numbers inherently present or obviously displayed in a phase diagram, but are rather products of complex algorithms required for the purposes of alloy design.

The above two examples show the three described steps proceeding in a linear fashion: calculation, extraction, and mining. However, as described previously one unique aspect of this invention above simply using CALPHAD via computer is the ability to design multiple alloys of unique microstructure and performance from the database of extracted thermodynamic quantities. For example, roughly 15,000 alloys were calculated in the above two examples and two thermodynamic quantities were described in each of the extraction steps. However, in this method it is advantageous to extract the full spectrum of the potential thermodynamic quantities during the extraction routine regardless of the intended design of the metallurgist at the time.

In the above two examples, a non-magnetic hardfacing material and a crack resistant hardfacing material were separately designed using the full 3 step process, calculation, extraction, and mining. In the proceeding examples, additional independent alloys can be designed without running additional calculations. This example shows the effectiveness of this method, whereby a metallurgist can execute uniquely separate design routines without running additional calculations or interfacing with phase diagrams.

Example 3: Selecting a Corrosion and Abrasion-Resistant Alloy Composition

Utilizing the previous 15,000 calculations, a metallurgist can immediately mine this data to develop a unique alloy system: abrasion and corrosion resistant hardfacing alloys. In this example, the extraction routine is rerun on the 15,000 alloys to include additional thermodynamic properties of interest that one skilled in the art has determined to be relevant to the desired microstructure and properties via experimental measurements. An example of an additional thermodynamic parameter to be added would be the Cr content in weight % in the austenite phase at 1300K, termed '1300K Austenite Cr'. Again the selection of this thermodynamic quantity is non-obvious and requires experiments in that the corrosion performance of the alloy is being correlated to the Cr content at high temperature (1300K) in a phase which does not exist in the alloy at room temperature (austenite). In this example, no calculation routine is run, and 15,000 alloys can be quickly interrogated for a unique alloy system. In example 3, the data extraction step is run to extract all of the thermodynamic quantities discusses thus far, $T(\gamma-\alpha)$, $\Sigma_{hard}$, primary, secondary, and 1300 Austenite Cr even though not all of these quantities are relevant to this particular example. Once extracted this data can be mined to determine the best alloy for this application. For example, all 15,000 alloys can be sorted to immediately remove any alloy which has a 1300 Austenite Cr level below 0.12. Then the remaining alloys can be ranked according to the highest secondary value. FIG. 9 is displays the extracted thermodynamic quantities for all 15,000 alloys to demonstrate how the design of such an alloy is quantified into simple numerical terms. However, as mentioned, no graphical display or evaluation of thermodynamic information is required to make this alloy design. Rather, a single alloys or collection of several alloys is selected for manufacture based on the algorithmic sorting and ranking routines.

The power of this method is revealed in that this alloy design was executed on 15,000 alloys without having to recalculate 15,000 alloys, which may take up to about 15 hours using a supercomputer. In the design process of Example 3, only the extraction process was run which may take up to around 1 hour. It can be appreciated that this method can be used to avoid prohibitive lengths of time such as 15,000 hours of calculation time for 15,000,00 alloys, allowing for this extremely large alloy set to be utilized in alloy design in about 100 hours.

Referring back to FIG. 6A, the chart 600 depicts the simultaneous evaluation of many alloys using two thermodynamic quantities simultaneously. In part this is done for matter of convenience because it is physically impossible to graphically display a series of alloys on a two dimensional plot for more than 2 thermodynamic quantities. However, this method is advantageous in its unique ability to evaluate a large set of alloys for more than 2 thermodynamic quantities. The numerical sorting and ranking algorithms allow an infinite number of thermodynamic quantities to be simultaneously considered, because at no point must a metallurgist review a phase diagram or other graphical display. It is often the case that multiple performance criteria must be met for the alloy to have utility as a manufactured product.

Example 4: Selecting a Non-Magnetic and Crack Resistant Alloy Composition

In another example the previous 15,000 calculations can be again utilized. In this case, the extraction routine is also avoided due to the extraction of the 5 thermodynamic criteria in the previous example despite only requiring two quantities for the design of the corrosion and abrasion resistant alloy. As thermodynamic criteria are continuously developed in this method, the calculation and extraction methods can be more often avoided to speed the process of alloy design. Referring back to FIG. 6B, the chart 620 illustrates an example chart used in mining a crack resistant non-magnetic hardbanding material. In this example, it was determined in a separate inventive step that the primary hard phase fraction and the T $\alpha$ to $\gamma$ transition temperature were relevant thermodynamic parameters for designing this product. The chart 620 of FIG. 6B then represents the mining results of the 15,000 alloys calculated in this particular example whereby these alloys are now evaluated for the non-magentic hardbanding application. In example 4, this uniquely and separate alloy design process was executed instantaneously as no additional calculation or extraction algorithms were run. Sorting and ranking are essentially instantaneous to the user even when designing within a very large number of alloys. It can appreciated in this example how an extremely large alloy set of 15,000,000 alloys can be utilized in alloy design in a matter of seconds using this disclosed method, whereas conventional CALPHAD techniques would require a prohibitively long 15,000 hrs (625 days or 1.7 years). However, this comparison is incorrect in that it requires one skilled in the art to evaluate and understand thermodynamic information contained in 15,000,000 phase diagrams, which cannot be executed via conventional CALPHAD. Thus, it can be appreciated that the simultaneous evaluation of 15,000,000 alloys via conventional CALPHAD methods is logistically impossible.

Similar to FIG. 6A, FIG. 6B depicts the simultaneous evaluation of many alloys using just two thermodynamic quantities due to the physical limitations of plotting multiple variables. However, it is often desirable to use 3 or more thermodynamic quantities in alloy design and Example 4 can further benefit from the use of additional thermodynamic quantities in its design. In Example 4 the ranking and sorting algorithms can be used to identify an alloy which contains a maximum 'T $\alpha$ to $\gamma$' threshold and which are further ranking according to the highest 'Primary' quantity. The design of the alloy can be further enhanced in this example by adding an additional criteria, 'Secondary'. In this case, the 'Secondary' quantity is sorted such that only alloys which have a maximum 'Secondary' quantity are further considered in the design. In this exemplary example, three thermodynamic criteria are simultaneously used in the design of the alloy set. It can be appreciated that is impossible to create a thermodynamic display of information using conventional CALPHAD methods whereby 3 independent variables can be used in design; such a display must be a three dimensional image and is prohibitively difficult to interpret. Furthermore, the physical display of more than three independent variables cannot be physically displayed. The disclosed method is the only known way to execute alloy design using more than 3 thermodynamic quantities simultaneously for a plurality of alloys.

In one embodiment, this method is used to evaluate 2 or more thermodynamic quantities of an alloy set. In a preferred embodiment, this method is used to evaluate 3 or more thermodynamic quantities of an alloy set. In a still preferred embodiment, this method is used to evaluate 4 or more thermodynamic quantities of an alloy set.

Example 3 and 4 highlight another unique characteristic of this method as compared to conventional CALPHAD, the capability to execute alloy design amongst vast compositional ranges effectively. In one embodiment, this method is unique in its ability to execute alloy design using 100 alloys simultaneously. In a preferred embodiment, this method is unique in its ability to execute alloy design using 500 alloys simultaneously. In a still preferred embodiment, this method is unique in its ability to execute alloy design using 1,000 alloys simultaneously. In the US 2009/0053100 A1 example, the CALPHAD method is used to effectively evaluate 1-4 alloys simultaneously. Conventional techniques using graphical displays of thermodynamic information are effective at evaluating 1-10 alloys, become increasingly ineffective when evaluating 11-99 alloys simultaneously, and become useless for alloy design when evaluation 100 alloys or more.

In another example, 1,000,000 alloys have been calculated and 50 thermodynamic criteria have been defined based on experimental measurements and their ability to predict microstructure and performance. Once calculated, which may take up to 6 months using a super computer, and extracted, which may take up to several weeks, the mining process can be executed to design multiple types of alloys. The mining process is essentially instantaneous utilizing a computer.

In another example, all possibilities of steel alloys, which represents trillions of potential alloy combinations, are calculated which may take up to several years utilizing a series of supercomputers. 100 relevant thermodynamic quantities are determined via 100 unique inventive process to predict a variety of microstructural and performance characteristics in steel. Once calculated and evaluated, this data can be mined and used to design alloys for a variety of different desired microstructural and performance criteria to develop unique and separate functional materials amongst the entire span of possible steels effectively instantaneously.

In a final example, all possible elemental combinations are calculated which may take up to a decade utilizing a series of supercomputers. 1,000 relevant thermodynamic quantities are determined via 1,000 unique inventive process to predict a variety of microstructural and performance characteristics. Once calculated and evaluated, this data can be mined and used to design alloys for a variety of different desired microstructural and performance criteria to develop unique and separate functional materials amongst the entire span of possible materials effectively instantaneously.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A method of visually outputting information regarding an alloy composition or compositions having a target property, the method comprising:
   extracting programmatically by a computing device comprising a microprocessor a plurality of thermodynamic quantities from thermodynamic phase data of a plurality of alloy compositions, wherein the thermodynamic phase data comprises data calculated by varying more than three independent variables that is incapable of being displayed as a two or three dimensional graphical image;
   electronically mining the thermodynamic quantities programmatically by the computing device to rank at least a subset of the plurality of alloy compositions based on a comparison of at least a subset of the thermodynamic quantities; and
   graphically representing a ranked subset of the plurality of alloy compositions based on the at least the subset of the thermodynamic quantities.

2. The method of claim 1, wherein graphically representing comprises plotting a two or three dimensional graphical image in which each of thermodynamic quantities is represented as an axis, and wherein plotted data points represent at least some of the alloy compositions.

3. The method of claim 1, wherein each of the plurality of alloy compositions has at least four alloying elements.

4. The method of claim 2, wherein the thermodynamic phase data is calculated by varying compositions of three or more of the at least four alloying elements over specified composition ranges.

5. The method of claim 1, wherein the independent variables include temperature and amounts of alloying elements of the plurality of alloy compositions.

6. The method of claim 1, wherein the extracted thermodynamic quantities are predetermined to be correlated to the target property.

7. The method of claim 1, further comprising electronically mining the thermodynamic quantities a second time programmatically by the computing device using the microprocessor to rank at least a second subset of the plurality of alloys based on a comparison of a second subset of the thermodynamic quantities, wherein the second subset of the thermodynamic quantities is predetermined to be correlated to a second target property different from the target property, and wherein electronically mining the second time is performed without additional thermodynamic phase data.

8. The method of claim 1, wherein graphically representing comprises plotting correlations between the at least the subset of the thermodynamic quantities.

9. An apparatus configured to visually output information regarding an alloy composition or compositions having a target property, the apparatus comprising:
   a computing device comprising a microprocessor;
   a thermodynamic phase data extraction module configured to extract programmatically by the computing device a plurality of thermodynamic quantities from thermodynamic phase data of a plurality of alloy compositions, wherein the thermodynamic phase data comprises data calculated by varying more than three independent variables that is incapable of being physically displayed in a two or three dimensional graphical image; and
   an electronic data mining module configured to electronically mine the thermodynamic quantities programmatically by the computing device using the microprocessor to rank at least a subset of the plurality of alloy compositions based on a comparison of at least a subset of the thermodynamic quantities,
   an output module configured to graphically represent a ranked subset of the alloy compositions based on the at least the subset of the thermodynamic quantities.

10. The apparatus of claim 8, wherein each of the plurality of alloy compositions has at least four alloying elements.

11. The apparatus of claim 9, wherein the thermodynamic phase data comprises data calculated by varying compositions of three or more of the at least four alloying elements over specified composition ranges.

12. The apparatus of claim 8, wherein the independent variables include temperature and concentrations of alloying elements of the plurality of alloy compositions.

13. The apparatus of claim 8, wherein the extracted thermodynamic quantities are predetermined to be correlated to the target property.

14. The apparatus of claim 8, wherein the output module is configured to graphically plot correlations between the at least the subset of the thermodynamic quantities.

15. A non-transitory computer-readable medium comprising instructions stored thereon that when executed cause a computing device to perform steps for visually outputting information regarding an alloy composition or compositions having a target property, the steps comprising:
   extracting programmatically by a computing device a plurality of thermodynamic quantities from thermodynamic phase data of a plurality of alloy compositions, wherein the thermodynamic phase data comprises data calculated by varying more than three independent variables that is incapable of being displayed as a two or three dimensional graphical image;
   electronically mining the thermodynamic quantities programmatically by the computing device using a microprocessor to rank at least a subset of the plurality of alloy compositions based on a comparison of at least a subset of the thermodynamic quantities; and graphically representing a ranked subset of the plurality of alloy compositions based on the at least the subset of the thermodynamic quantities.

16. The non-transitory computer-readable medium of claim 14, wherein each of the plurality of alloy compositions has at least four alloying elements.

17. The non-transitory computer-readable medium of claim 15, wherein the thermodynamic phase data comprises data calculated by varying compositions of three or more of the at least four alloying elements over specified composition ranges.

18. The non-transitory computer-readable medium of claim 14, wherein the independent variables include temperature and concentrations of alloying elements of the plurality of alloy compositions.

19. The non-transitory computer-readable medium of claim 14, wherein the steps further comprise electronically mining the thermodynamic quantities a second time programmatically by the computing device using the microprocessor to rank at least a second subset of the plurality of alloys based on a comparison of a second subset of the thermodynamic quantities, wherein the second subset of the thermodynamic quantities is predetermined to be correlated to a second target property different from the target property, and wherein electronically mining the second time is performed without additional thermodynamic phase data.

20. The non-transitory computer-readable medium of claim 14, wherein graphically representing comprises plotting correlations between the at least the subset of the thermodynamic quantities.

* * * * *

UNITED STATES PATENT AND TRADEMARK OFFICE
CERTIFICATE OF CORRECTION

Page 1 of 2

PATENT NO. : 10,495,590 B2
APPLICATION NO. : 15/887867
DATED : December 3, 2019
INVENTOR(S) : Kenneth Vecchio et al.

It is certified that error appears in the above-identified patent and that said Letters Patent is hereby corrected as shown below:

On the Title Page

On Page 3, Column 1, Item (56), Line 35, under Other Publications, change "nirtide" to --nitride--.

On Page 3, Column 1, Item (56), Line 46, under Other Publications, change "Opinon" to --Opinion--.

On Page 3, Column 2, Item (56), Line 13, under Other Publications, change "Quatum" to --Quantum--.

On Page 3, Column 2, Item (56), Line 18, under Other Publications, change "Cromium," to --Chromium,--.

In the Drawings

On Sheet 4 of 12, Reference Number (454), FIG. 4, Line 2, change "Soldify" to --Solidify--.

On Sheet 4 of 12, Reference Number (456), FIG. 4, Line 3, change "Soldify" to --Solidify--.

On Sheet 7 of 12, FIG. 6A, y-axis, Line 1, change "Austentite" to --Austenite--.

In the Specification

In Column 11, Line 62 (Approx.), change "Soldify" to --Solidify--.

In Column 12, Line 67, change "the a" to --the--.

In Column 16, Line 50, change "the a" to --a--.

Signed and Sealed this
Twenty-sixth Day of May, 2020

Andrei Iancu
*Director of the United States Patent and Trademark Office*

CERTIFICATE OF CORRECTION (continued)
U.S. Pat. No. 10,495,590 B2

In Column 25, Line 33, change "that that" to --that--.

In Column 31, Line 25, change "non-magentic" to --non-magnetic--.